US009546261B2

(12) United States Patent
Dicke et al.

(10) Patent No.: US 9,546,261 B2
(45) Date of Patent: Jan. 17, 2017

(54) STABILIZING OF ORGANIC MATERIAL WITH AMINO-TRIAZINE BASED MANNICH-COMPOUNDS

(71) Applicant: Borealis AG, Vienna (AT)

(72) Inventors: Rene Dicke, Leonding (AT); Andreas Meinecke, Linz (AT); Christian Paulik, Linz (AT); Klaus Bretterbauer, Linz (AT); Helmut Puchinger, Freistadt (AT); Jingbo Wang, Linz (AT); Clemens Schwarzinger, Wels (AT)

(73) Assignee: Borealis AG, Vienna (AT)

( * ) Notice: Subject to any disclaimer, the term of this patent is extended or adjusted under 35 U.S.C. 154(b) by 123 days.

(21) Appl. No.: 14/346,508

(22) PCT Filed: Sep. 20, 2012

(86) PCT No.: PCT/EP2012/068474

§ 371 (c)(1),
(2) Date: Mar. 21, 2014

(87) PCT Pub. No.: WO2013/041592

PCT Pub. Date: Mar. 28, 2013

(65) Prior Publication Data

US 2014/0235766 A1 Aug. 21, 2014

(30) Foreign Application Priority Data

Sep. 23, 2011 (EP) .................................... 11182450

(51) Int. Cl.

*C08K 5/3492* (2006.01)
*C07D 251/48* (2006.01)
*C07D 251/70* (2006.01)

(52) U.S. Cl.

CPC ......... *C08K 5/34922* (2013.01); *C07D 251/48* (2013.01); *C07D 251/70* (2013.01)

(58) Field of Classification Search

CPC . C08K 5/34922; C07D 251/48; C07D 251/70; C08L 23/02

(Continued)

(56) References Cited

U.S. PATENT DOCUMENTS 4,284,790 A 8/1981 Hinsken et al.
4,297,492 A * 10/1981 Rasberger .......... C08G 73/0644 524/100

(Continued)

FOREIGN PATENT DOCUMENTS

DE 4316611 A1 11/1993
DE 4316622 A1 11/1993

(Continued)

OTHER PUBLICATIONS

Hensen et al., Handbook of Plastic Extrusion Technology, 1989, 3-7, Germany. Abstract.

(Continued)

*Primary Examiner* — Susannah Chung
*Assistant Examiner* — Josephine Chang
(74) *Attorney, Agent, or Firm* — The Webb Law Firm

(57) ABSTRACT

Use of one or more amino-triazine based Mannich-compounds and/or their dimers or trimers and/or one or more precondensate therefrom, including special new amino-triazine based Mannich-compounds, as antioxidant and/or UV-stabilizer for organic material, preferably for polymers; the stabilized material and use of the stabilized material.

12 Claims, 1 Drawing Sheet

OIT at 220°C (TRM-AO is the antioxidant of Example 2)

(58) Field of Classification Search
USPC .......................... 524/100; 544/197, 196, 208
See application file for complete search history.

(56) References Cited

U.S. PATENT DOCUMENTS

| | | | |
|---|---|---|---|
| 4,325,863 | A | 4/1982 | Hinsken et al. |
| 4,338,244 | A | 7/1982 | Hinsken et al. |
| 5,175,312 | A | 12/1992 | Dubs et al. |
| 5,216,052 | A | 6/1993 | Nesvadba et al. |
| 5,252,643 | A | 10/1993 | Nesvadba |
| 5,356,966 | A | 10/1994 | Nesvadba |
| 5,367,008 | A | 11/1994 | Nesvadba |
| 5,428,162 | A | 6/1995 | Nesvadba |
| 5,428,177 | A | 6/1995 | Nesvadba |
| 5,488,117 | A | 1/1996 | Nesvadba |
| 6,140,326 | A | 10/2000 | Lazzari et al. |
| 2002/0016389 | A1 | 2/2002 | Dongiovanni et al. |
| 2005/0143500 | A1 | 6/2005 | Gugumus |

FOREIGN PATENT DOCUMENTS

| | | | | |
|---|---|---|---|---|
| DE | 4316876 | A1 | | 11/1993 |
| EP | 0589839 | A1 | | 3/1994 |
| EP | 0591102 | A1 | | 4/1994 |
| EP | 0782994 | A1 | | 7/1997 |
| EP | 2332926 | A1 | | 6/2011 |
| GB | 1244685 | | | 9/1971 |
| GB | 2301106 | A | | 11/1996 |
| JP | 48033770 | B | * | 10/1973 |
| JP | 2009173845 | A | | 8/2009 |
| WO | 2011061220 | A1 | | 5/2011 |

OTHER PUBLICATIONS

Maciejewski et al., Highly branched melamine-phenolic novolaks, Polymer Bulletin, 2002, pp. 251-259, 48.

* cited by examiner

OIT at 220°C (TRM-AO is the antioxidant of Example 2)

FIGURE 2: Viscosity measurements

Compositions C1, C2, C3, C4, C7, C10 and C13 as defined in Table 2

STABILIZING OF ORGANIC MATERIAL WITH AMINO-TRIAZINE BASED MANNICH-COMPOUNDS

CROSS-REFERENCE TO RELATED APPLICATIONS

This application is the United States national phase of International Application No. PCT/EP2012/068474 filed Sep. 20, 2012 and claims priority to European Patent Application No. 11182450.4 filed Sep. 23, 2011, the disclosures of which are hereby incorporated in their entirety by reference.

BACKGROUND OF THE INVENTION

Field of the Invention

The present invention relates to the use of special amino-triazine based Mannich-compounds for increasing the resistance of organic material, preferably polymer, against degradation caused by oxidation; to organic material, preferably polymers, with increased resistance to oxidation and to the use of the polymers, with increased resistance to oxidation for producing articles.

Description of Related Art

It is known that the mechanical, chemical and/or aesthetic properties of inanimate organic materials, especially of polymeric materials, worsen under the influence of energy such as heat and/or sunlight and other sources of ultraviolet (UV) radiation, and/or oxygen. This results in an irreversible deterioration of the chemical and/or physical properties of the non-living organic materials, e.g. results for polymeric materials i.a. in a loss of strength, stiffness and flexibility, discoloration and scratching and loss of gloss.

Such aging processes are normally based on oxidation reactions which are caused by heat, light, mechanical stress, catalysis or reactions with impurities. The aging of polymeric materials can occur during their production, during processing into shaped parts by moulding, extrusion, etc. and/or during use of the shaped parts.

It is well-known in the art that stabilizers, such as antioxidants and light stabilizers can prevent or at least reduce these effects by adding them to the polymers to protect them during processing and to achieve the desired end-use properties.

Stabilizers, like antioxidants, traditionally and currently used comprise sterically hindered phenolics, aromatic amines, hindered amine stabilizers, organo-phosphites/phosphonites and thioethers. However, appropriate combinations of stabilizers have to be carefully selected, depending on the desired final properties, the polymeric article should have.

Antioxidants interrupt the degradation process in different ways, depending on their structure. The two major classifications are chain terminating primary antioxidants and hydroperoxide decomposing secondary antioxidants. Primary antioxidants react rapidly with peroxy radicals and are therefore called "radical scavengers". The majority of primary antioxidants for polyolefins are sterically hindered phenols.

Low volatility is an important characteristic of stabilizers used in any applications where high temperatures are encountered. High temperatures are used in the processing of thermoplastics and in the curing of thermoset resins and coatings. High temperatures are also often present in the end-use applications for the stabilized material. Low volatility will prevent loss of the stabilizer during processing, curing, and high temperature end-uses.

Besides reducing losses of stabilizer during processing or curing, low volatility will minimize processing problems such as die lip build-up and plate-out.

Stabilizers known from the state of the art have a number of disadvantages. A major disadvantage is the frequently insufficient duration of the protective effect. A further disadvantage is the often poor synthetic accessibility of many stabilizers.

Many stabilizers migrate out of the polymer substrate to be protected, or are adsorbed (chemically or physically) by one or more systems components (such as pigments), thereby diminishing their effectiveness. Such migration and adsorption problems are examples of the general problems of lack of solubility and compatibility found for many commercial polymer additives.

Migration behavior of stabilizers added to polyolefin-based materials is dependent from a number of different properties such as diffusion rate of the molecules within the polymer matrix, chemical stability of the additives, type of additive decomposition products, etc. It has to be taken into account that an improvement in migration behavior must not be obtained on the expense of stabilization of the polymer matrix. Thus, providing an additive composition of low migration tendency is not straight-forward but rather needs a careful selection of appropriate compounds.

Thus there is still a demand for improved stabilizers, especially antioxidants which show improved properties, like low volatility, low migration tendency, high solubility, long-term stabilization, and the like.

Furthermore the antioxidant should lead to a high resistance of the stabilized polymers against oxidative degradation as measured in terms of oxidation induction times (OIT).

The object of the present invention is therefore to find suitable compounds showing all the desired properties, which can be used as antioxidants for organic materials, especially for polymers.

SUMMARY OF THE INVENTION

This object was achieved by using special amino-triazine based Mannich-compounds which increase the resistance of organic material, preferably polymer, against degradation caused by oxidation.

Therefore the present invention relates to the use of one or more amino-triazine based Mannich-compounds of the formula (I) and/or their dimers or trimers and/or one or more precondensate therefrom of the formula (II)

(I)

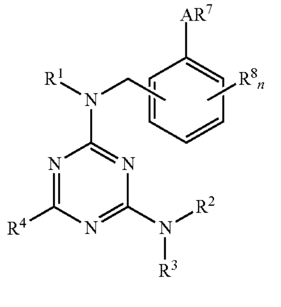

-continued (II)

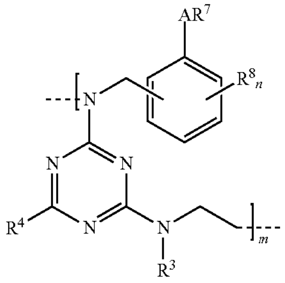

whereby

A is O, N or S $R^4$ is hydrogen, or $Q^1$, or a group $R^5$—N—$R^6$ bonded with its central nitrogen atom to the triazine ring of structure (I) or (II)

$R^1$, $R^2$, $R^3$, $R^5$ and $R^6$ are hydrogen, or $Q^1$ or group of the formula (III)

(III)

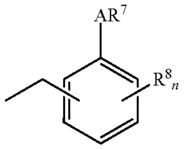

$R^7$ is hydrogen, or $Q^1$, whereby in case of A being O or $SR^7$ is present once, and in case of A being $NR^7$ is present twice, $R^8$ is selected independently from each other and can be $Q^1$, or is selected from a group comprising substituted or non-substituted hydroxy, substituted or non-substituted amino, halogen, substituted or non-substituted sulphur, or can be a group with the structure of (IV), whereby $R^{8'}$ has the meaning of $R^8$ (IV)

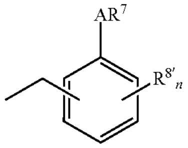

n is 0 to 4, $Q^1$ is selected from a group comprising substituted and non-substituted, linear or branched $C_1$-$C_{50}$-alkyl, substituted and non-substituted, linear or branched $C_2$-$C_{50}$-alkenyl, substituted and non-substituted, linear or branched $C_2$-$C_{50}$-alkinyl, substituted and non-substituted $C_3$-$C_{10}$-cycloalkyl, substituted and non-substituted $C_5$-$C_7$-cycloalkenyl, substituted and non-substituted $C_6$-$C_{20}$-aryl, which in each case can be interrupted by one or more atoms or group selected from oxygen atoms, sulphur atoms, substituted or mono-substituted nitrogen atoms, double bonds, siloxan groups and/or by one or more groups of the type —C(O)O—, —OC(O)—, —C(O)—, —C(O)NH—, —NHC(O)O—, —OC(O)NH—, —NHC(O)NH— and/or —OC(O)O—, whereby in case of $R^4$ the atoms and groups selected from oxygen atoms, sulphur atoms, —OC(O)—, —C(O)—, —NHC(O)O—, —NHC(O)NH— or —OC(O)O— can be directly connected to the triazine ring and in case of $R^7$ the atoms and groups selected from —C(O)—, C(O)O— or —C(O)NH— can be directly connected to A and in case of $R^8$ the groups selected from —OC(O)—, —C(O)—, —NHC(O)O—, —NHC(O)NH—, —C(O)O—, —C(O)NH— or —OC(O)O— can be directly connected to the aromatic ring, m is 2 to 20, as antioxidant for organic materials.

In case of $R^4$ being a group $R^5$—N—$R^6$ the amino-triazine based Mannich-compounds are melamine based Mannich-compounds.

Melamine based Mannich-compounds and their precondensates which can be used as antioxidants for organic materials according to the present invention are known and are described in WO 2011/061220. The melamine based Mannich-compounds are used according to WO 2011/061220 as additives for aldehyde scavenging, in particular formaldehyde scavenging, curing acceleration of resins, in particular urea-formaldehyde glues and/or melamine-formaldehyde resins, and as additive for improving swelling behaviour and thermo-mechanical properties of particle boards, laminates and wood composites. Their precondensates are used according to WO 2011/061220 in glues, prepregs recipes, for as cured resins in moulding compounds, in particular as covering for brakes and clutches or for commutators in electrical motors, and in laminates or as components in flame retardant systems.

In case of $R^4$ being H or $Q^1$ the amino-triazine based Mannich-compounds and their precondensates are new.

Thus the present invention also relates to amino-triazine based Mannich-compounds of formula (I), their dimers and trimers and their precondensates of formula (II) as such, wherein in the formulas (I) and (II) $R^4$ is H or $Q^1$; and $R^1$, $R^2$, $R^3$, $R^7$, $R^8$, A, $Q^1$, n and m are defined as described above.

In formula (I) to formula (IV) of the compounds being suitable antioxidants according to the present invention A is preferably O or N, more preferably A is O $R^4$ is preferably a group $R^5$—N—$R^6$ with $R^5$ and $R^6$ independently selected from hydrogen, substituted or unsubstituted, linear or branched $C_1$-$C_{12}$-alkyl, substituted and non-substituted $C_3$-$C_7$cycloalkyl and substituted and non-substituted, linear or branched $C_2$-$C_{12}$-alkenyl, preferably from H, methyl, ethyl, iso-propyl, n-butyl or sec-butyl; or from a group of formula (III) or $R^4$ is $Q^1$ with $Q^1$ being selected from substituted or unsubstituted, linear or branched $C_1$-$C_{18}$-alkyl, preferably from H, methyl, n-butyl, tert-butyl, lauryl, stearyl, substituted and non-substituted $C_6$-$C_{10}$-aryl, preferably substituted and non-substituted phenyl, more preferably unsubstituted phenyl.

$R^1$, $R^2$ and $R^3$ are preferably independently selected from H, substituted and non-substituted, linear or branched $C_1$-$C_{18}$-alkyl, substituted and non-substituted $C_3$-$C_7$cycloalkyl and substituted and non-substituted, linear or branched $C_2$-$C_{12}$-alkenyl, preferably from H, methyl, ethyl, propyl, butyl, lauryl or stearyl, or from a group of formula (III).

$R^7$ is preferably selected from H or $C_1$-$C_{12}$-alkyl which can be interrupted by one or more oxygen atoms, substituted or mono-substituted nitrogen atoms, and/or by one or more groups of the type —C(O)O—, —OC(O)— and —C(O)—, or the group —C(O)— can be directly connected to A.

n is preferably 1 or 2, whereby the preferred position of n is ortho to $AR^7$.

$R^8$ is preferably independently selected from a group comprising —OH, —$OCH_3$, —$OC_2H_5$, —$NH_2$, substituted or non-substituted, linear or branched $C_1$-$C_{12}$-Alkyl, in particular methyl, ethyl and tert.-butyl, substituted and non-substituted $C_3$-$C_7$-cycloalkyl and substituted and non-substituted, linear or branched $C_2$-$C_{12}$-alkenyl, substituted and non-substituted $C_6$-$C_{12}$ Aryl, in particular —$C_6H_5$, —$C_6H_4OH$, —$CH_2C_6H_5$, —$C(CH_3)_2C_8H_5$ or —$CH_2C_8H_4OH$, in particular —$CH_2C_8H_4OH$ as ortho- and/or para-isomers, more preferably $R^8$ is independently selected from the group comprising —OH, —$OCH_3$, —$OC_2H_5$, methyl, ethyl and tert.-butyl, most preferably $R^8$ is tert.-butyl.

m is preferably 2 to 10.

The term "substituted" in connection to alkyl, alkenyl, alkinyl, cycloalkenyl and aryl relates to the substitution of one or more atoms, usually H-atoms, by one or more of the following substituents: halogen, hydroxy, protected hydroxy, oxo, protected oxo, $C_3$-$C_7$-cycloalkyl, phenyl, naphtyl, amino, protected amino, primary or secondary amino, heterocyclic ring, imidazolyl, indolyl, pyrrolidinyl, $C_1$-$C_{12}$-alkoxy, $C_1$-$C_{12}$-acyl, $C_1$-$C_{12}$-acyloxy, nitro, carboxy, carbamoyl, carboxamid, N—($C_1$-$C_{12}$-alkyl)carboxamid, N,N-Di($C_1$-$C_{12}$-alkyl)carboxamid, cyano, methylsulfonylamino, thiol, $C_1$-$C_{10}$-alkylthio und $C_1$-$C_{10}$-alkylsulfonyl. The substituted groups can be once or twice substituted with same or different substituents.

The term "substituted" in connection to mercapto, hydroxy and amino relates to the substitution of at least one H atom by one or in case of amino one or two of one of the substituents mentioned above, in particular substituted and non-substituted, linear or branched $C_1$-$C_{12}$-alkyl, substituted and non-substituted $C_3$-$C_7$-cycloalkyl and substituted and non-substituted, linear or branched $C_2$-$C_{12}$-alkenyl. Hence, the mercapto and hydroxy group can be present as a mercaptoether or an ether group, respectively. Amino group can be present as a primary or secondary amine.

The term "substituted" in connection to a carbonyl group relates to —COR groups whereby R can have the meaning of one of the above substituents, in particular H, substituted and non-substituted, linear or branched $C_1$-$C_{12}$-alkyl, substituted and non-substituted $C_3$-$C_7$-cycloalkyl and substituted and non-substituted, linear or branched $C_2$-$C_{12}$-alkenyl.

The term "alkinyl" as used herein relates to a moiety of the formulae R—C≡C—, in particular to a linear or branched $C_2$-$C_{50}$-alkinyl. Examples for $C_2$-$C_{50}$-alkinyle comprise ethinyl, propinyl, 2-butinyl, 2-pentinyl, 3-pentinyl, 2-hexinyl, 3-hexinyl, 4-hexinyl, 2-heptinyl, 3-heptinyl, 4-heptinyl, 5-heptinyl, octinyl, noninyl, decinyl, undecinyl, dodecinyl, as well as di- and tri-ines of straight or branched alkyl chains.

The term "alkyl" relates to moieties like methyl, ethyl, n-propyl, isopropyl, n-butyl, isobutyl, s-butyl, t-butyl, amyl, t-amyl, hexyl, heptyl, octyl, nonyl, decyl, undecyl, dodecyl, and alike. Preferred alkyl groups are methyl, ethyl, isobutyl, s-butyl, t-butyl und isopropyl.

The term "oxo" relates to a carbon atom, which is connected with an oxygen atom via a double bond whereby a keto or an aldehyde group is formed. The term "protected oxo" relates to a carbon atom, which is substituted by two alkoxy groups or is connected twice with a substituted diol forming a non-cyclic or cyclic ketal group.

The term "alkoxy" relates to moieties like methoxy, ethoxy, n-propoxy, isopropoxy, n-butoxy, t-butoxy and alike. A preferred alkoxy group is methoxy.

The term "$C_3$-$C_7$-cycloalkyl" comprises groups like cyclopropyl, cyclobutyl, cyclopentyl, cyclohexyl und cycloheptyl. The term "$C_5$-$C_7$-Cycloalkenyl" relates to a 1,2 or 3-cyclopentenyl ring, a 1,2,3 or 4-cyclohexenyl ring or a 1,2,3,4 or 5-cycloheptenylring.

In a preferred embodiment of the present invention the compounds have one of the following structures:

(1)

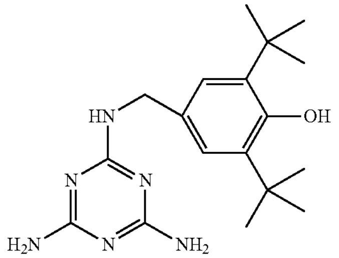

(2)

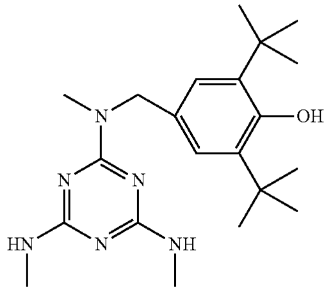

(3)

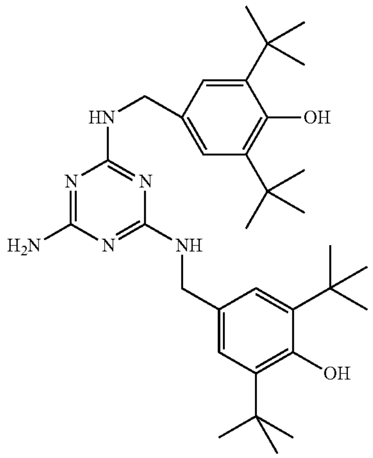

-continued
(4)
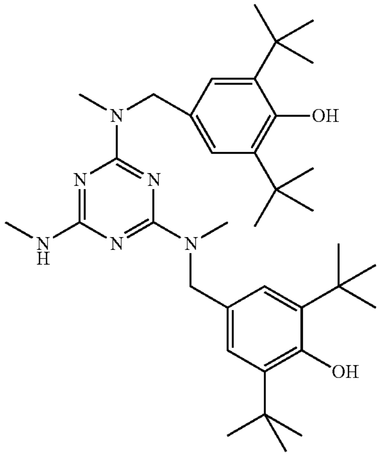
(5)
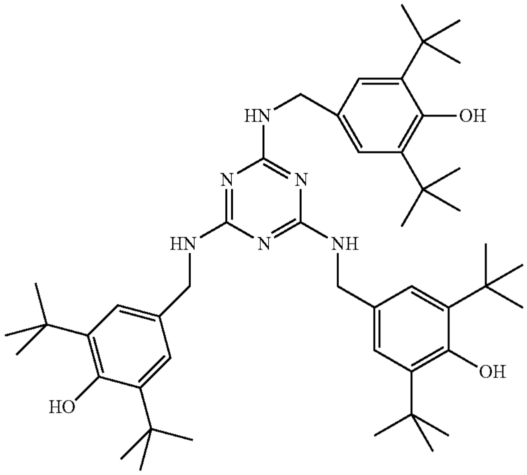
(6)
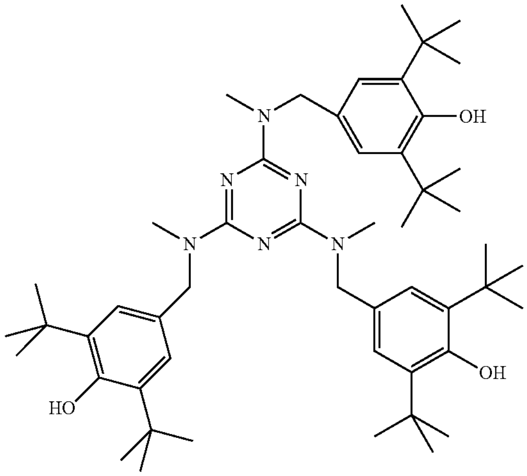
-continued
(7)
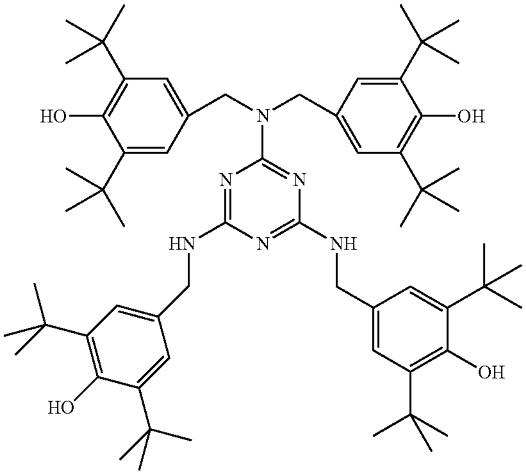
(8)
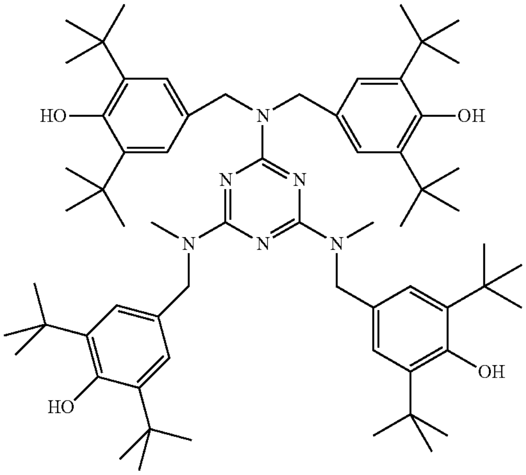
(9)
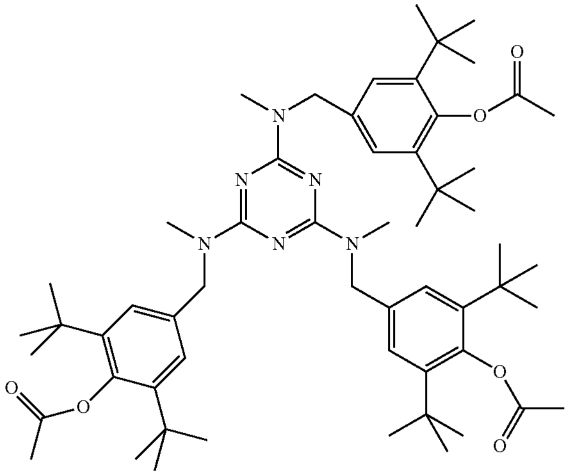

-continued
(10)
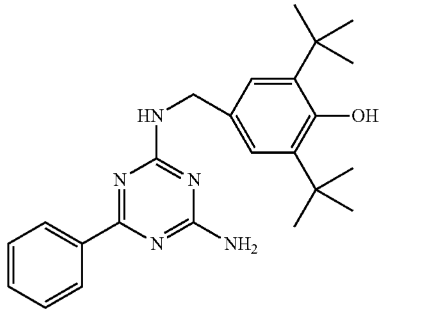
(11)
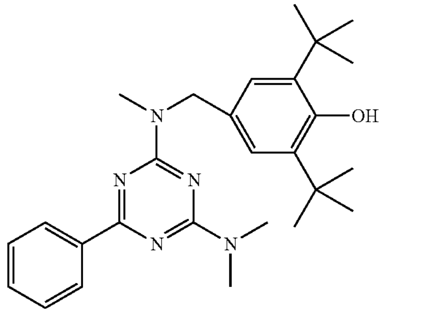
(12)
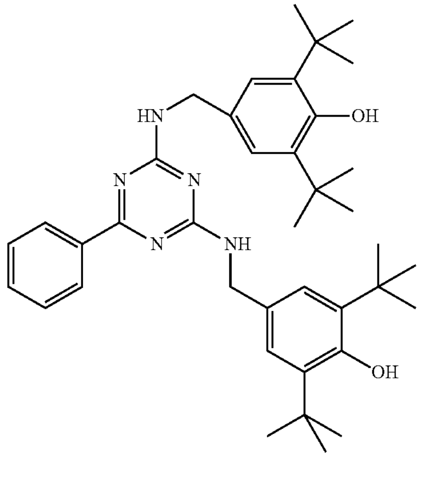
(13)
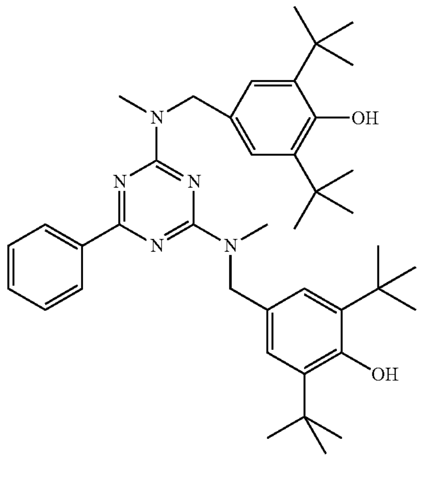
-continued
(14)
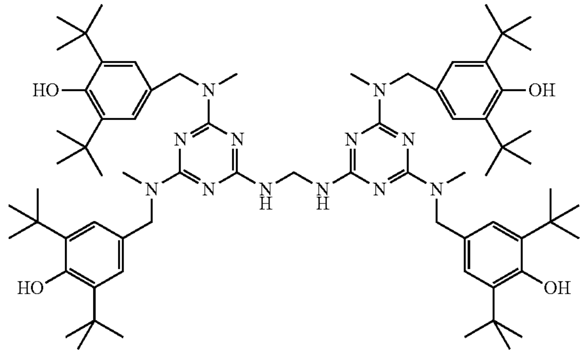
(15)
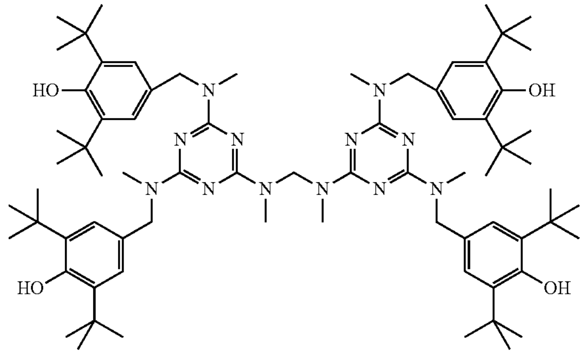
(16)
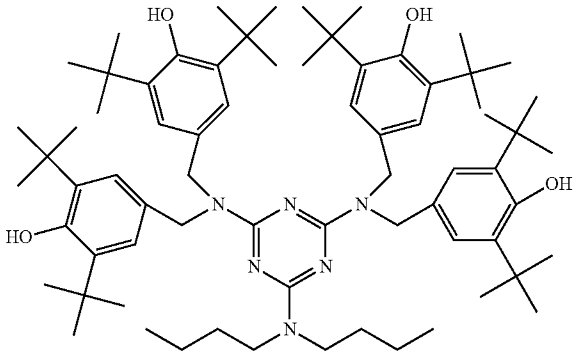
(17)
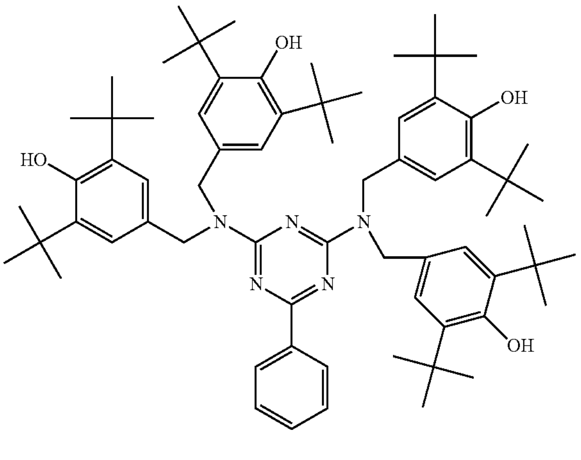

-continued (18)

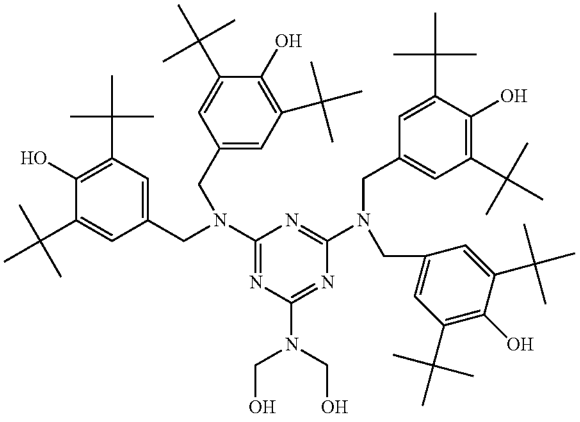

or mixtures therefrom.

The amino-triazine based Mannich compounds, suitable as antioxidants according to the invention, can be also described as co-condensation products of amino-triazine, like melamine, and phenol and formaldehyde. These products are especially interesting, since they are of a white colour and also do not change their appearance during further condensation. In contrast, typical phenol resins are a dark-red to black colour.

The preparation of the melamine based Mannich compounds with $R^4$ being $R^5$—N—$R^6$, suitable as antioxidants according to the invention, is described in WO 2011/061220.

The amino-triazine based Mannich compounds with $R^4$ being H or $Q^1$, suitable as antioxidants according to the invention, are prepared analogous thereto.

The production process comprises a) the reaction of at least one amino-triazine derivate of formula (V) with formaldehyde under basic conditions to form at least one compound of formula (VI)

(formula V)

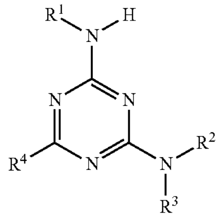

(formula VI)

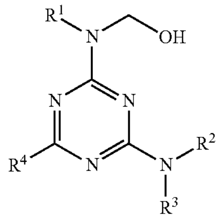

b) reacting the at least one compound of formula (VI) in the presence of a catalyst to form at least one Mannich-base of formula (VII)

(formula VII)

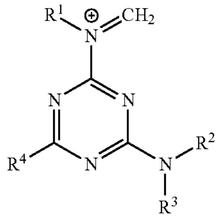

c) reacting the at least one Mannich-base of formula (VII) with at least one substituted or non-substituted aromatic compound of the general formulae (VIII) to form at least one of the compounds according to the general formula (I)

(formula VIII)

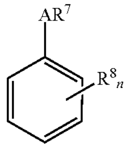

d) and working up the reaction mixture, whereby the moieties $R^1$ to $R^8$, n and A have the above meanings.

In this process the formation of Iminium-ion as the Mannich base in step b) is the rate-determining step. The electrophilic Iminium-ion is formed in situ by protonation of the OH-containing compound obtained in step a) followed by dehydration. In general, the Iminium-ion is stabilised in a protic polar solvent, whereas in an unpolar solvent the stability of the Iminium-ion is reduced and thus reacts faster.

It is to be understood that the process steps can be carried out in form of a one-pot synthesis or independently from each other. This means that for instance the OH-containing compounds of step a) can be are separately synthesized, isolated and stored before further usage.

The preferred molar ratio of amino-triazine derivative to aromatic compound of formula (VIII) in the process is from 1:1 to 1:6, preferably from 1:1 to 1:4, in particular preferred from 1:1 to 1:3.

Step a) of the process is carried out at a pH between 8 and 12, preferably between 9 and 11, in the presence of an inorganic or organic base, preferably $K_2CO_3$, $Na_2CO_3$, $Ca(OH)_2$, NaOH and/or KOH.

Steps b) and c) are preferably carried out at a pH between 1 and 6, preferably 2 and 5, most preferably between 2 and 4.

The catalyst used in steps b) or c) is preferably selected from a group comprising sulphonic acid, sulphuric acid, trifluoracetic acid (TFAA), 4-toluenesulphonic acid (pTSA), monochloracetic acid (MCAA), glacial acetic acid, hydrochloric acid and formic acid. The molar excess of the catalyst varies dependent of the applied acid and can be between 1:10, preferably 1:5, in particular preferably 1:3, in respect to the Mannich base of formula (VII). However, the reaction can also be carried out using catalytic amounts of acid.

The process enables the formation of mono-, twice-, three- and four-times substituted co-condensation amino-triazine products. Also dimers and trimers are formed.

The amino-triazine based co-condensation products can be reacted further with formaldehyde, giving rise to precondensates of formula (II).

The precondensate can be of course also available as mixtures of different precondensates.

The detailed reaction conditions are described in WO 2011/061220.

BRIEF DESCRIPTION OF THE DRAWINGS

The foregoing summary, as well as the following detailed description, will be better understood when read in conjunction with the appended drawings. In the drawings:

FIG. 2 is a graph representing viscosity measurements for compositions C1, C2, C3, C4, C7, C10, and C13 as defined in Table 2.

DESCRIPTION OF THE INVENTION

Figure 1:
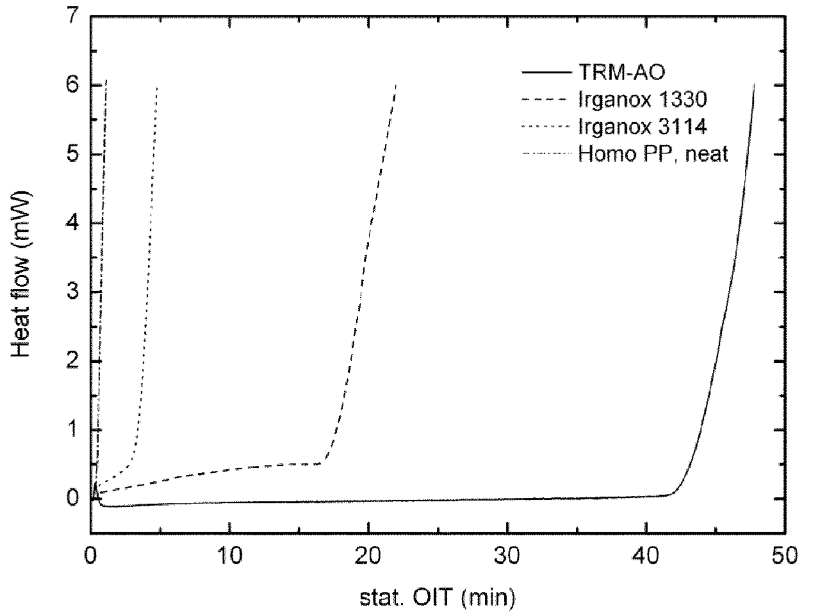
FIG. 1 is a graph representing the heat flow in function of Oxidation Induction Time Variant 1 at 220° C. for TRM-AO, Irganox 1330, Irganox 3114, and neat Homo PP.
Figure 1:
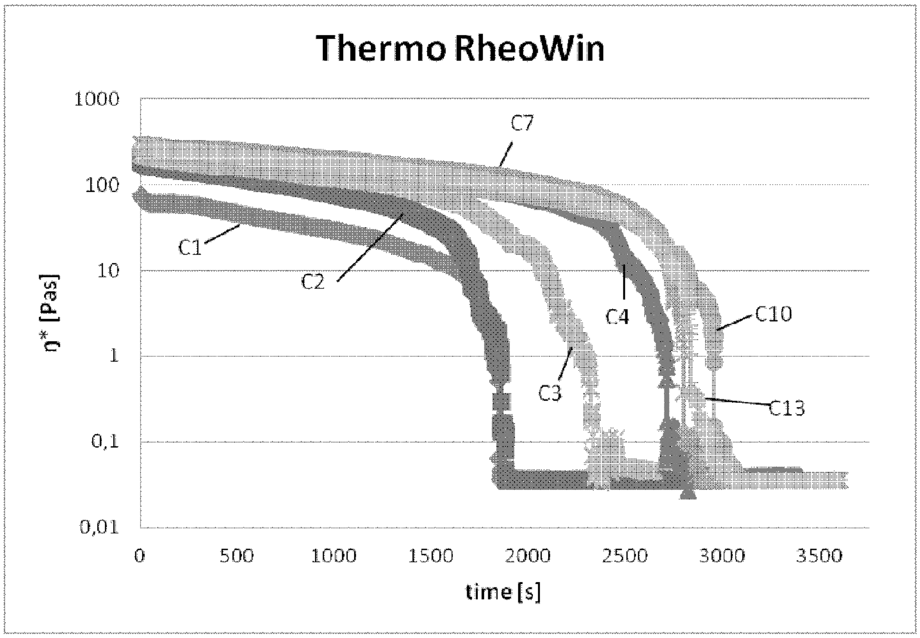

As mentioned above the described amino-triazine based Mannich-compounds of the formula (I), their dimers or trimers and precondensate therefrom of the formula (II) can be used alone or as a mixture, such as a mixture of two or more amino-triazine based Mannich-compounds of the formula (I), a mixture of amino-triazine based Mannich-compounds of the formula (I) with dimers and/or trimers, or as a mixture of one or more amino-triazine based Mannich-compounds of the formula (I) with a precondensate of formula (II), and the like, as antioxidant for organic material, preferably polymers.

The amino-triazine based Mannich-compounds of the formula (I), their dimers or trimers and precondensate therefrom of the formula (II) are particularly useful as antioxidant for stabilizing a wide variety of organic materials including, for example, organic compounds, oils, fuel, like jet fuel, fats, waxes, cosmetics, dyes and biocides, and particularly various organic polymers (both cross-linked and non-cross-linked) used in applications such as photographic materials, plastics, films, fibers or dyed fibers, rubbers, paints and other coatings, and adhesives.

The present invention, consequently, also relates to a method of stabilizing an organic material against oxidative degradation (e.g., an organic material such as an organic polymer in the form of a film, fiber, shaped article or coating) by incorporating into said material an amount of an amino-triazine based Mannich-compounds of the formula (I), their dimers or trimers and precondensate therefrom of the formula (II) or mixtures therefrom effective to stabilize.

Preferably the organic materials to be stabilized are polymers as for example:

1. Polymers of monoolefins and diolefins, for example polypropylene, polyisobutylene, polybut-1-ene, poly-4-methylpent-1-ene, polyisoprene or polybutadiene, as well as polymers of cycloolefins, for example of cyclopentene or norbomene; furthermore polyethylene (which optionally can be crosslinked); for example, high density polyethylene (HDPE), polyethylene of high density and high molar mass (HDPE-HMW), polyethylene of high density and ultrahigh molar mass (HDPE-UHMW), medium density polyethylene (HMDPE), low density polyethylene (LOPE), linear low density polyethylene (LLDPE), branched low density polyethylene (BLDPE).

Polyolefins, i.e. polymers of monoolefins exemplified in the preceding paragraph, in particular polyethylene and polypropylene, can be prepared by various, and especially by the following, methods:

a) free-radical polymerization (normally under high pressure and at elevated temperature)

b) catalytic polymerization using a catalyst that normally contains one or more metals of group IVb, Vb, VIb or VIII of the Periodic Table. These metals usually have one or more ligands, such as oxides, halides, alcoholates, esters, ethers, amines, alkyls, alkenyls and/or aryls that may be either p- or s-coordinated. These metal complexes may be in the free form or fixed on substrates, for example on activated magnesium chloride, titanium(III) chloride, alumina or silicon oxide. These catalysts may be soluble or insoluble in the polymerization medium. The catalysts can be active as such in the polymerization or further activators may be used, for example metal alkyls, metal hydrides, metal alkyl halides, metal alkyl oxides or metal alkyloxanes, the metals being elements of groups Ia, IIa and/or IIIa of the Periodic Table. The activators may be modified, for example, with further ester, ether, amine or silyl ether groups. These catalyst systems are usually termed Phillips, Standard Oil Indiana, Ziegler-Natta, TNZ (DuPont), metallocene or single site catalysts (SSC).

2. Mixtures of the polymers mentioned under 1), for example mixtures of polypropylene with polyisobutylene, polyethylene with polyisobutylene, polypropylene with polyethylene (for example PP/HDPE/LDPE) and mixtures of different types of polyethylene (for example LDPE/HDPE) with one another.

3. Copolymers of monoolefins and diolefins with each other or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide or ethylene-acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned under 1), for example polypropylene-ethylene-propylene copolymers, LDPE-ethylene-vinyl acetate copolymers, LDPE-ethylene-acrylic acid copolymers, LLDPE-ethylene-vinyl acetate copolymers, LLDPE-ethylene-acrylic acid copolymers and alternating or random polyalkylenecarbon monoxide copolymers and mixtures thereof with other polymers, for example polyamides.

4. Hydrocarbon resins (for example C5-C9) including hydrogenated modifications thereof (e.g. tackifier resins) and mixtures of polyalkylenes and starch.

5. Polystyrene, poly(p-methylstyrene), poly(a-methylstyrene).

6. Copolymers of styrene or a-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methacrylate; mixtures of high impact strength of styrene copolymers and another polymer, for example a polyacrylate, a diene polymer or an ethylene-propylene-diene terpolymer; and block copolymers of styrene, such as styrene-butadiene-styrene, styrene-isoprene-styrene, styrene-ethylene/butylene-styrene or styrene-ethylene/propylene-styrene.

7. Graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 6), for example the copolymer mixtures known as ABS, MBS, ASA or AES polymers.
8. Halogen-containing polymers, such as polychloroprene, chlorinated rubber, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; as well as copolymers thereof such as vinyl chloride-vinylidene chloride, vinyl chloride-vinyl acetate or vinylidene chloride-vinyl acetate.
9. Polymers derived from alpha, beta-unsaturated acids and derivatives thereof, such as polyacrylates and polymethacrylates, polyacrylonitriles, polyacrylamides and polymethyl methacrylates impact-modified with butyl acrylate.
10. Copolymers of the monomers mentioned under 9) with each other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.
11. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in section 1.
12. Homopolymers and copolymers of cyclic ethers, such as polyalkylene glycols, polyethylene oxide, polypropylene oxide or copolymers thereof with bisglycidyl ethers.
13. Polyacetals such as polyoxymethylene and those polyoxymethylenes which contain comonomers, for example ethylene oxide; polyacetals modified with thermoplastic polyurethanes, acrylates or MBS.
14. Polyphenylene oxides and sulfides, and mixtures thereof with styrene polymers or polyamides.
15. Polyurethanes derived from hydroxyl-terminated polyethers, polyesters and polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, such as polyamide 4, 6, 6/6, 6/10, 6/9, 6/12, 4/6, 12/12, 11 and 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. As well as polyamides or copolyamides modified with EPDM or ABS; and polyamides condensed during processing (RIM polyamide systems).
17. Polyureas, polyimides, polyamide-imides, polyether imides, polyester amides, polyhydantoins and polybenzimidazoles.
18. Polyesters derived from dicarboxylic acids and dialcohols and/or from hydroxycarboxylic acids or hydroxyalkanoates or the corresponding lactones, such as polyethylene terephthalate, polybutylene terephthalate, poly-1,4-dimethylolcyclohexane terephthalate, polyhydroxybenzoates, polyhydroxybutyrate as well as block polyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, bisphenol, furan, acetophenone, guanamin, urea or melamine on the other hand, such as phenol/formaldehyde resins, urea/formaldehyde resins and melamine/formaldehyde resins as examples.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example from epoxy acrylates, urethane acrylates or polyester acrylates.
25. Alkyd resins, polyester resins and acrylic resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, examples being products of bisphenol A diglycidyl ethers, bisphenol F diglycidyl ethers, which are crosslinked by means of customary hardeners, such as anhydrides or amines, for example, with or without accelerators.
27. Natural polymers such as cellulose, natural rubber, gelatin and derivatives thereof which have been chemically modified in a polymer-homologous manner, for example cellulose acetates, cellulose propionates and cellulose butyrates, or the cellulose ethers such as methyl cellulose; as well as rosins and derivatives.
28. Mixtures (polyblends) of the aforementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/MBS, PPO/HIPS, PPO/PA 6.6 and copolymers, PA/HDPE, PA/PP, PA/PPO, PBT/ABS or PBT/PET/PC.
29. Natural and synthetic organic substances which constitute pure monomeric compounds or mixtures thereof, examples being mineral oils, animal or vegetable fats, oils and waxes, or oils, waxes and fats based on synthetic esters (e.g. phthalates, adipates, phosphates or trimellitates), and also blends of synthetic esters with mineral oils in any desired proportion by weight, as are employed, for example, as spin finishes, and aqueous emulsions thereof.

30. Aqueous emulsions of natural or synthetic rubbers, such as natural rubber latex or latices of carboxylated styrene-butadiene copolymers.

In addition, the present invention also relates to a polymer composition, preferably a thermoplastic polymer composition, comprising a polymer base resin (A) and an antioxidant (B) selected from an amino-triazine based Mannich-compounds of the formula (I), their dimers or trimers and precondensate therefrom of the formula (II) or mixtures.

Antioxidant (B) is preferably contained in the composition in an amount of up to 5000 ppm, more preferably 300 ppm up to 2000 ppm and still more preferably 500 ppm up to 1500 ppm, based on the total composition. Higher amounts can also be added if suitable.

The term "base resin" denotes the entirety of polymeric components in the polymer composition, preferably in the thermoplastic polymer composition, according to the invention, usually making up at least 90 wt % of the total composition.

The favourable effect of the antioxidants according to the present invention is not dependent on the type polymer base resin used. The base resin may therefore be any polymer or polymer composition as described above.

Preferably the polymer base resin comprises a thermoplastic polymer, more preferably the polymer base resin comprises a polyolefin as described above in paragraph (1) to (3), even more preferably an ethylene homo- or copolymer or a propylene homo- or copolymer or mixtures thereof. The polyolefin can be unimodal or multimodal, like bi- or trimodal.

In a further embodiment of the present invention the compounds selected from a amino-triazine based Mannich-compounds of the formula (I), their dimers or trimers and precondensate therefrom of the formula (II) or mixtures therefrom are used as UV-stabilizers for organic materials.

Thus the present invention also relates to a method of stabilizing an organic material against degradation caused by UV radiation (e.g., an organic material such as an organic polymer in the form of a film, fiber, shaped article or coating) by incorporating into said material an amount of an amino-triazine based Mannich-compounds of the formula (I), their dimers or trimers and precondensate therefrom of the formula (II) or mixtures therefrom effective to stabilize.

In addition, the present invention also relates to a polymer composition, preferably a thermoplastic polymer composition, comprising a polymer base resin (A) and an UV-stabilizer (C) selected from an amino-triazine based Mannich-compounds of the formula (I), their dimers or trimers and precondensate therefrom of the formula (II) or mixtures therefrom.

UV-stabilizer (C) is preferably contained in the composition in an amount of 5000 ppm or less, more preferably 2000 ppm or less and most preferably 1000 ppm or less, based on the total composition.

In an additional embodiment of the present invention the compounds selected from an amino-triazine based Mannich-compounds of the formula (I), their dimers or trimers and precondensate therefrom of the formula (II) or mixtures therefrom are used as antioxidants as well as UV-stabilizers for organic materials.

Thus the present invention also relates to a method of stabilizing an organic material against oxidative degradation and degradation caused by UV radiation (e.g., an organic material such as an organic polymer in the form of a film, fiber, shaped article or coating) by incorporating into said material an amount of an amino-triazine based Mannich-compound of the formula (I), their dimers or trimers and precondensate therefrom of the formula (II) or mixtures therefrom effective to stabilize.

In addition, the present invention also relates to a polymer composition, preferably a thermoplastic polymer composition, comprising a polymer base resin (A) and a combined antioxidant/UV-stabilizer (D) selected from an amino-triazine based Mannich-compound of the formula (I), their dimers or trimers and precondensate therefrom of the formula (II) or mixtures therefrom.

Combined antioxidant/UV-stabilizer (D) is preferably contained in the composition in an amount of 10000 ppm or less, more preferably 4000 ppm or less, still more preferably 2000 ppm or less, still more preferably 1000 ppm or less, and most preferably 600 ppm or less, based on the total composition.

Depending upon their ultimate end use, the amino-triazine based Mannich-compounds of the formula (I), their dimers or trimers and precondensate therefrom of the formula (II) or mixtures therefrom of the present invention may be combined with a variety of additives conventionally employed in the antioxidant and/or UV stabilizing art, such as (further) antioxidants, (further) UV absorbers and stabilizers, metal deactivators, antistatics, phosphites and phosphonites, hydroxylamines, nitrones, thiosynergists, co-stabilizers, nucleating agents, fillers and reinforcing agents, plasticizers, lubricants, emulsifiers, pigments, rheological additives, catalysts, level agents, optical brighteners, flameproofing agents, anti-static agents and blowing agents.

Examples are listed below:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(a-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1-yl)phenol, 2,4-dimethyl-6-(1'-methyl-tridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecyl-thiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tertbutyl-4-ethylphenol), 2,2'-methylenebis[4-methyl-6-(α-methylcyclo-hexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(a-methylbenzyl)-4-nonylphenol], 2,2'-methylenebis[6-(α,α-dimethylbenzyl)-4-nonyl-phenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methyl-phenyl)butane, 1,1-bis(5-tert-butyl-4-hydroxy-2-methylphenyl)-3-n-dodecylmercapto-butane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxy-phenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxy-dibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, like dioctadecyl-2,2-bis(3,5-di-tert-butyl-2-hydroxy-benzyl)malonate, di-octadecyl-2-(3-tert-butyl-4-hydroxy-5-methylbenzyl)-malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tertbutyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)-isocyanurate, 2,4,6-tris-(3,5-di-tert-butyl-4-hydroxyphenylethyl)-1,3,5-triazine, 1,3,5-tris(3,5-di-tertbutyl-4-hydroxypheny)propionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzyl-phosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methyl-benzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)-propionyloxy}-1,1-dimethylethyl]-2,4,8,10-tetraoxa-spiro[5.5]undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of b-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl) trimethylenediamide, N,N'-bis(3,5-di-tert-butyl-4-hydroxy-phenylpropionyl)hydrazide, N,N'-bis[2-(3-[3,5-di-tert-butyl-4-hydroxyphenyl]-propionyl-oxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylene-diamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylene-diamine, N-cyclohexyl-N'-phenyl-p-phenylenediamine, 4-(p-toluene-sulfamoyl)diphenylamine, N,N'-dimethyl-N,N'-di-secbutyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoyl-aminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diamino-diphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1,3'-dimethylbutyl)phenyl]amine, tert-octylated N-phenyl-1-naphthylamine, a mixture of mono- and dialkylated tert-butyl/tert-octyldiphenylamines, a mixture of mono and dialkylated nonyldiphenylamines, a mixture of mono- and dialkylated dodecyl-diphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-(1,1,3,3-tetramethylbutyl)phenyl)benzotriazole, 2-(2'-hydroxy-4'-octyloxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzo-triazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)-benzo-triazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)-carbonyl-ethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethyl-butyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

$$[R—CH_2CH_2—COO—CH_2CH_2 \rfloor_2,$$

where R=3'-tert-butyl-4'-hydroxy-5'-2H-benzotriazol-2-ylphenyl, 2-[2'-hydroxy-3'-(,-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-decyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenylsalicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbo-methoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)-sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethyl-piperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis(3-aminopropyl-amino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione, 5-(2-ethylhexanoyl)-oxymethyl-3,3,5-trimethyl-2-morpholinone, 1-(2-hydroxy-2-methylpropoxy)-4-octadecanoyl-oxy-2,2,6,6-tetramethylpiperidine,1,3,5-tris(N-cyclohexyl-N-(2,2,6,6-tetramethyl-piperazin-3-on-4-yl)amino)-s-triazine, 1,3,5-tris(N-cyclohexyl-N-(1,2,2,6,6-pentamethyl-piperazin-3-on-4-yl)amino)-s-triazine, the reaction product of 2,4-bis[(1-cyclohexyloxy-2,2,6,6-piperidin-4-yl)butylamino]-6-chloro-s-triazine with N,N'-bis(3-aminopropyl)-ethylenediamine), a mixture of 4-hexadecyloxy- and 4-stearyloxy-2,2,6,6-tetramethylpiperidine, a condensate of N,N'-bis(2,2,6,6-tetramethyl-4-piperidyl)-hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6- tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide; N-(1,2,2,6,6-pentamethyl-4-piperidyl)-n-dodecylsuccinimide; 2-undecyl-7,7,9,9-tetramethyl-1-oxa-3,8-diaza-4-oxo-spiro[4,5]decane; 5-(2-ethylhexanoyl)oxymethyl-3,3,5-trimethyl-2-morpholinone; a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylamino-propyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. Further 2-(2-Hydroxyphenyl)-1,3,5-triazines, for example 2,4,6-tris(2-hydroxy-4-octyloxyphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,35-triazine, 2-[2-hydroxy-4-(2-hydroxy-3-butyloxypropoxy) phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-methoxyphenyl)-4,6-Biphenyl-1,3,5-triazine, 2,4,6-tris [2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenyl-propionyl)-hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyldihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritoldiphosphite, diisodecyloxypentaerythritol diphosphite, bis(2,4-di-tert-butyl-6-methylphenyl)pentaerythritoldiphosphite, bis(2,4,6-tris(tert-butyl-phenyl)pentaerythritol diphosphite, tristearyl sorbitol triphosphite, tetrakis(2,4-di-tert-butyl-phenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-dibenz[d,g]-1,3,2-dioxaphosphocin, 2,2',2''-nitrilo-[triethyltris-(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butyl-phenoxy)-1,3,2-dioxaphosphirane.

The following phosphites are especially preferred:

Tris(2,4-di-tert-butylphenyl)phosphite (Irgafos®168, Ciba-Geigy), tris(nonylphenyl) phosphite, (A)

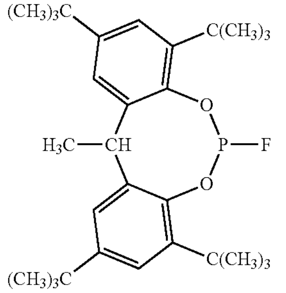

(B)

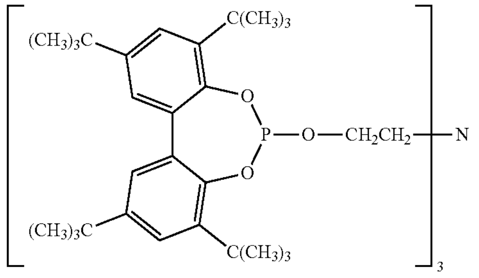

(C)

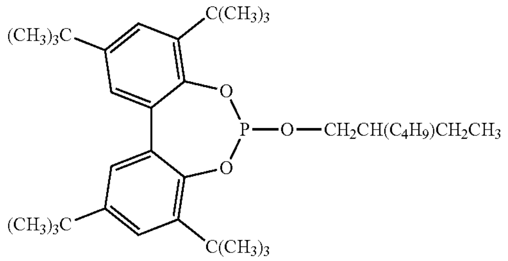

(D)

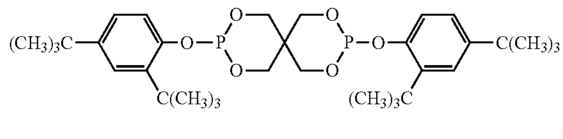

-continued (E)

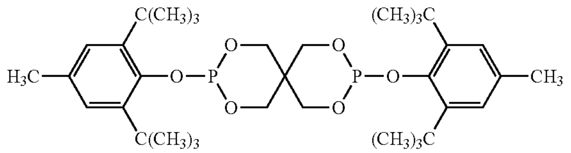

(F)

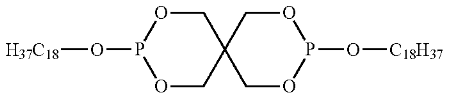

(G)

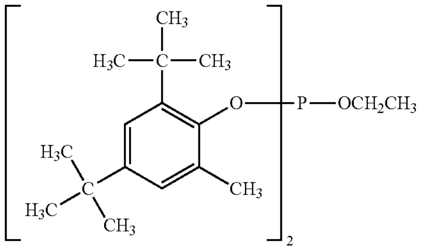

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.
6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxylamine derived from hydrogenated tallow amine.
7. Thiosynergists, for example dilauryl thiodipropionate or distearyl thiodipropionate.
8. Peroxide scavengers, for example esters of -thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis($\alpha$-dodecylmercapto)propionate.
9. Polyamide stabilisers, for example copper salts in combination with iodides and/or phosphorus compounds and salts of divalent manganese.
10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.
11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.
12. Fillers and reinforcing agents, for example calcium carbonate, silicates, alumosilicates, organo-modified alumosilicates, glass fibres, glass bulbs, asbestos, talc, kaolin, mica, barium sulfate, metal oxides and hydroxides, carbon black, graphite, wood flour and flours or fibers of other natural products, synthetic fibers.
13. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxy-ethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tertbutylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.
14. Antistatics selected for example from fatty acid esters, like Glycerol mono stearate (GMS); Ethoxylated alkylamines, like ethoxylated tertiary amines, Ethoxylated tertiary fatty amines; Ethoxylated amides and Sorbitan based products; like Sorbitan stearate Sorbitan monooleate; alkylsulfonates or alkylphophates.

In yet another embodiment of the present invention the amino-triazine based Mannich-compounds of the formula (I), their dimers or trimers and precondensate therefrom of the formula (II) or mixtures therefrom are used as antioxidant for organic material, preferably for thermoplastic polymers, in combination with a hindered amine light stabilizers (HALS).

The HALS is preferably selected from 1) 4-hydroxy-2,2,6,6-tetramethylpiperidine
2) 1-allyl-4-hydroxy-2,2,6,6-tetramethylpiperidine
3) 1-benzyl-4-hydroxy-2,2,6,6-tetramethylpiperidine
4) 1-(4-tert-butyl-2-butenyl)-4-hydroxy-2,2,6,6-tetramethylpiperidine
5) 4-stearoyloxy-2,2,6,6-tetramethylpiperidine
6) 1-ethyl-4-salicyloyloxy-2,2,6,6-tetramethylpiperidine
7) 4-methacryloyloxy-1,2,2,6,6-pentamethylpiperidine
8) 1,2,2,6,6-pentamethylpiperidin-4-yl-(3,5-di-tert-butyl-4-hydroxyphenyl)propionate
9) di(1-benzyl-2,2,6,6-tetramethylpiperidin-4-yl) maleate
10) di(2,2,6,6-tetramethylpiperidin-4-yl) succinate
11) di(2,2,6,6-tetramethylpiperidin-4-yl) glutarate
12) di(2,2,6,6-tetramethylpiperidin-4-yl) adipate
13) di(2,2,6,6-tetramethylpiperidin-4-yl) sebacate
14) di(1,2,2,6,6-pentamethylpiperidin-4-yl) sebacate
14a) a mixture comprising 20% b.w. of (1,2,2,6,6-pentamethylpiperidin-4-yl) (methyl) sebacate and 80% by weight of di(1,2,2,6,6-pentamethylpiperidin-4-yl)sebacate
15) di(1,2,3,6-tetramethyl-2,6-diethyl-piperidin-4-yl) sebacate
16) di(1-allyl-2,2,6,6-tetramethylpiperidin-4-yl) phthalate
17) 1-hydroxy-4-cyanoethoxy-2,2,6,6-tetramethylpiperidine
18) 1-acetyl-2,2,6,6-tetramethylpiperidin-4-yl acetate
19) tri(2,2,6,6-tetramethylpiperidin-4-yl)trimellitate 20) 1-acryloyl-4-benzyloxy-2,2,6,6-tetramethylpiperidine 21) di(2,2,6,6-tetramethylpiperidin-4-yl) diethylmalonate 22) di(1,2,2,6,6-pentamethylpiperidin-4-yl)dibutylmalonate 23) di(1,2,2,6,6-pentamethylpiperidin-4-yl)butyl(3,5-di-tert-butyl-4-hydroxybenzyl) malonate 24) di(1-octyloxy-2,2,6,6-tetramethylpiperidin-4-yl) sebacate 25) di(1-cyclohexyloxy-2,2,6,6-tetramethylpiperidin-4-yl) sebacate 26) hexane-1',6'-bis(4-carbamoyloxy-1-n-butyl-2,2,6,6-tetramethylpiperidine)

27) toluene-2',4'-bis-(4-carbamoyloxy-1-n-propyl-2,2,6,6-tetramethylpiperidine)

28) dimethylbis(2,2,6,6-tetramethylpiperidin-4-oxy)silane 29) phenyltris(2,2,6,6-tetramethylpiperidin-4-oxy)silane 30) tris(1-propyl-2,2,6,6-tetramethylpiperidin-4-yl)phosphite 30-a) tris(1-methyl-2,2,6,6-tetramethylpiperidin-4-yl)phosphite 31) tris(1-propyl-2,2,6,6-tetramethylpiperidin-4-yl)phosphate 32) phenyl bis(1,2,2,6,6-pentamethylpiperidin-4-yl)phosphonate 33) 4-hydroxy-1,2,2,6,6-pentamethylpiperidine 34) 4-hydroxy-N-hydroxyethyl-2,2,6,6-tetramethylpiperidine 35) 4-hydroxy-N-(2-hydroxypropyl)-2,2,6,6-tetramethylpiperidine 36) 1-glycidyl-4-hydroxy-2,2,6,6-tetramethylpiperidine 36-a-1) 1,2,3,4-tetrakis[2,2,6,6-tetramethylpiperidin-4-yloxycarbonyl]butane 36-a-2) bis[2,2,6,6-tetramethylpiperidin-4-yloxycarbonyl]-bis[tridecyloxycarbonyl]butane 36-b-1) 1,2,3,4-tetrakis[12,2,6,6-pentamethylpiperidin-4-yloxycarbonyl]butane 36-b-2) bis[1,2,2,6,6-pentamethylpiperidin-4-yloxycarbonyl]-bis[tridecyloxycarbonyl]butane 36-c) 2,2,6,6-tetramethylpiperidin-4-yloxycarbonyl(C15-C17alkane)

36-d)

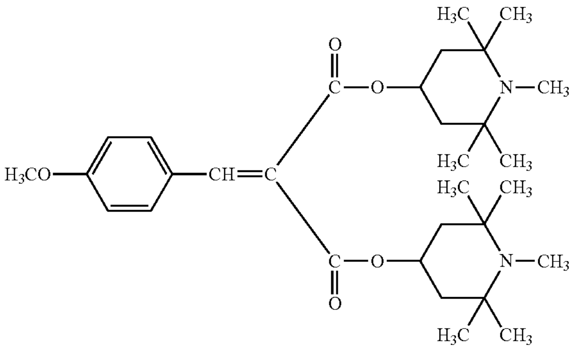

36-e)

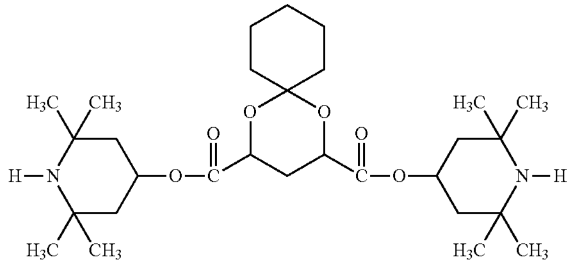

37) N,N'-bis(2,2,6,6-tetramethylpiperidin-4-yl)hexamethylene-1,6-diamine

38) N,N'-bis(2,2,6,6-tetramethylpiperidin-4-yl)hexamethylene-1,6-diacetamide 39) bis(2,2,6,6-tetramethylpiperidin-4-yl)amine 40) 4-benzoylamino-2,2,6,6-tetramethylpiperidine 41) N,N'-bis(2,2,6,6-tetramethylpiperidin-4-yl)-N,N'-dibutyladipamide 42) N,N'-bis(2,2,6,6-tetramethylpiperidin-4-yl)-N,N'-dicyclohexyl-2-hydroxypropylene-1,3-diamine 43) N,N'-bis(2,2,6,6-tetramethylpiperidin-4-yl)-p-xylylenediamine 44) N,N'-bis(2,2,6,6-tetramethylpiperidin-4-yl)succinamide 45) bis(2,2,6,6-tetramethylpiperidin-4-yl)N-(2,2,6,6-tetramethylpiperidin-4-yl)-α-aminodipropionate

46)

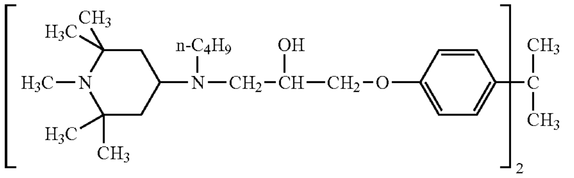

47) 4-(bis-2-hydroxyethylamino)-1,2,2,6,6-pentamethylpiperidine 48) 4-(3-methyl-4-hydroxy-5-tent-butyl-benzamido)-2,2,6,6-tetramethylpiperidine 49) 4-methacrylamido-1,2,2,6,6-pentamethylpiperidine 49-a-1)

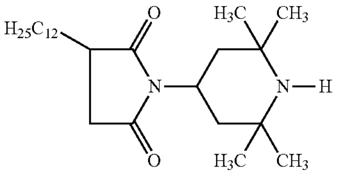

49-a-2)

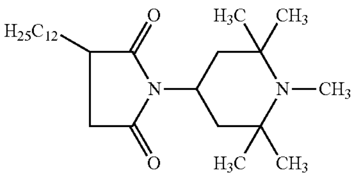

49-a-3)

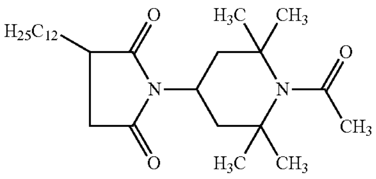

49-b) N,N',N''-tris[2,2,6,6-tetramethylpiperidin-4-ylamino (2-hydroxypropylene)]isocyanurate 49-c) 2-(2,2,6,6-tetramethylpiperidin-4-ylamino)-2-(2,2,6,6-tetramethylpiperidin-4-yl-amino-carbonyl)propane 49-d) 1,6-bis[N-(2,2,6,6-tetramethylpiperidin-4-yl)formylamino]hexane 49-e) 1-(2,2,6,6-tetramethylpiperidin-4-ylamino)-2-(2,2,6,6-tetramethylpiperidin-4-yl-amino-carbonyl)ethane 50) 9-aza-8,8,10,10-tetramethyl-1,5-dioxaspiro[5.5]undecane
51) 9-aza-8,8,10,10-tetramethyl-3-ethyl-1,5-dioxaspiro[5.5]undecane
52) 8-aza-2,7,7,8,9,9-hexamethyl-1,4-dioxaspiro[4.5]decane
53) 9-aza-3-hydroxymethyl-3-ethyl-8,8,9,10,10-pentamethyl-1,5-dioxaspiro[5.5]undecane
54) 9-aza-3-ethyl-3-acetoxymethyl-9-acetyl-8,8,10,10-tetramethyl-1,5-dioxaspiro[5.5]-undecane
55) 2,2,6,6-tetramethylpiperidine-4-spiro-2'-(1',3'-dioxane)-5'-spiro-5"-(1",3"-dioxane)-2"-spiro-4'"-(2'",2'",6'",6'"-tetramethylpiperidine)
56) 3-benzyl-1,3,8-triaza-7,7,9,9-tetramethylspiro[4.5]decane-2,4-dione
57) 3-n-octyl-1,3,8-triaza-7,7,9,9-tetramethylspiro[4.5]decane-2,4-dione
58) 3-allyl-1,3,8-triaza-1,7,7,9,9-pentamethylspiro[4.5]decane-2,4-dione
59) 3-glycidyl-1,3,8-triaza-7,7,8,9,9-pentamethylspiro[4.5]decane-2,4-dione
60) 1,3,7,7,8,9,9-heptamethyl-1,3,8-triazaspiro[4.5]decane-2,4-dione
61) 2-isopropyl-7,7,9,9-tetramethyl-1-oxa-3,8-diaza-4-oxospiro[4.5]decane
62) 2,2-dibutyl-7,7,9,9-tetramethyl-1-oxa-3,8-diaza-4-oxospiro[4.5]decane
63) 2,2,4,4-tetramethyl-7-oxa-3,20-diaza-21-oxodispiro[5.1.11.2]heneicosane
64) 2-butyl-7,7,9,9-tetramethyl-1-oxa-4,8-diaza-3-oxospiro[4.5]decane
65) 8-acetyl-3-dodecyl-1,3,8-triaza-7,7,9,9-tetramethylspiro[4.5]decane-2,4-dione

66)

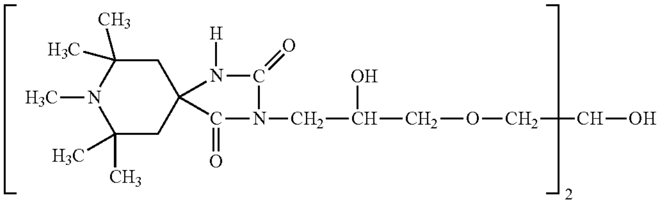

67)

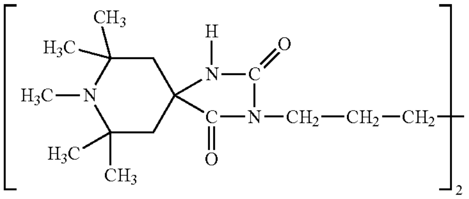

68)

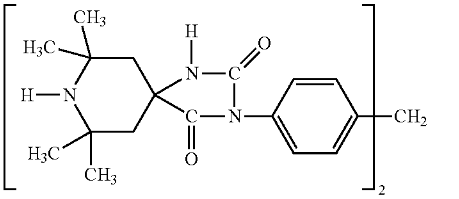

69-a)

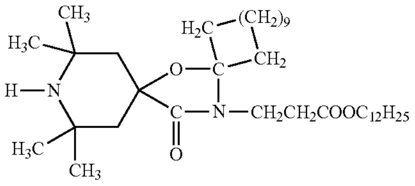

69-b) mixture of 60% by weight of

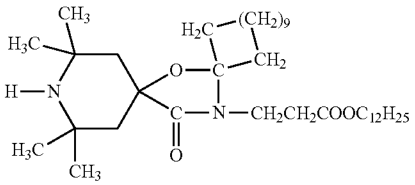

and 40% by weight of

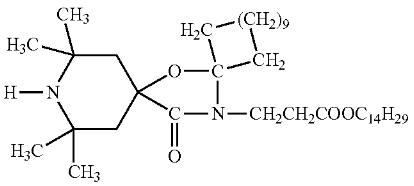

-continued
70)
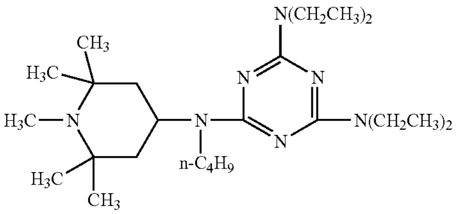
71)
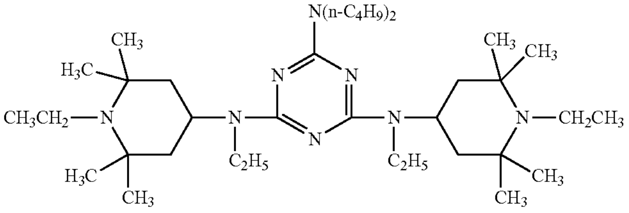
72)
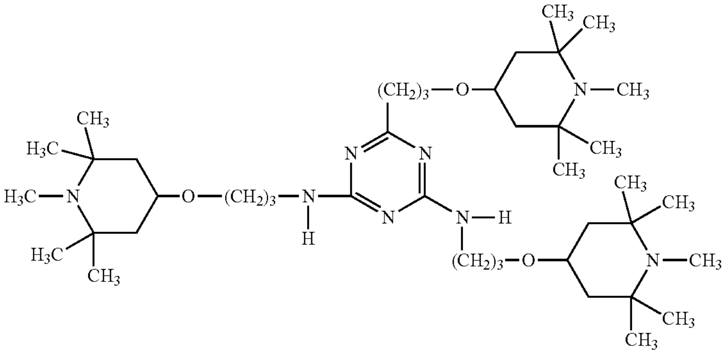
73)
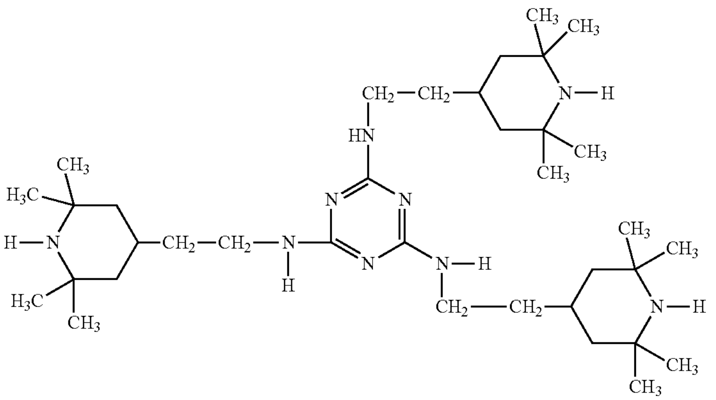
74)
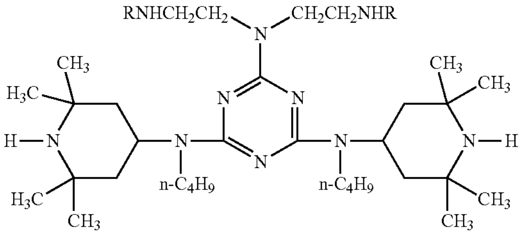
where R is
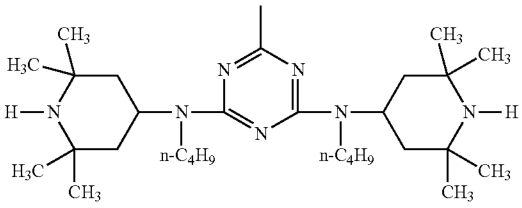

-continued
75)
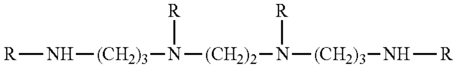
where R has the same meaning as in compound 74
76)
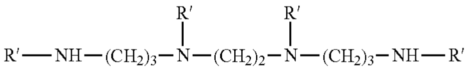
where R′ is
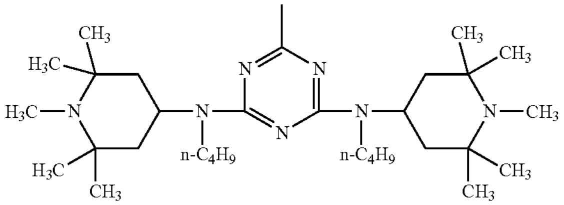
77)
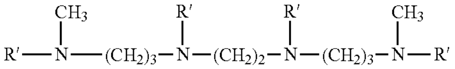
where R′ has the same meaning as in compound (76)
78)
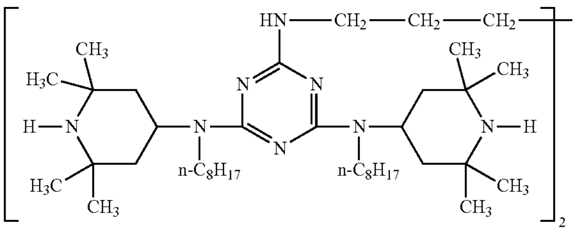
79)
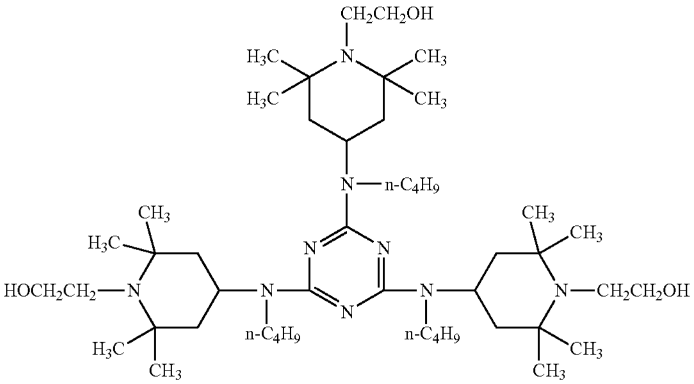
80)
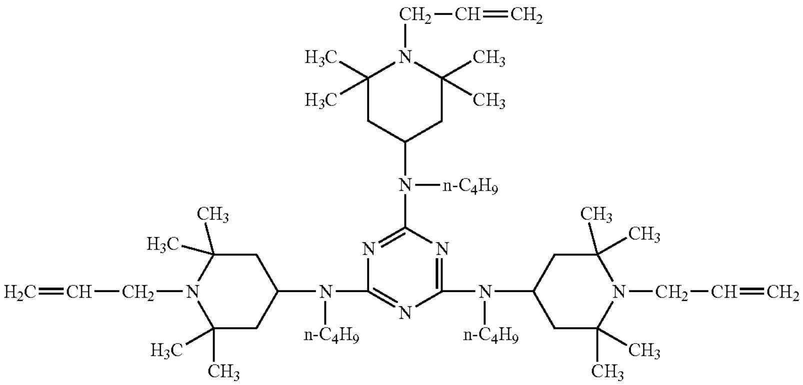

-continued 80-1)

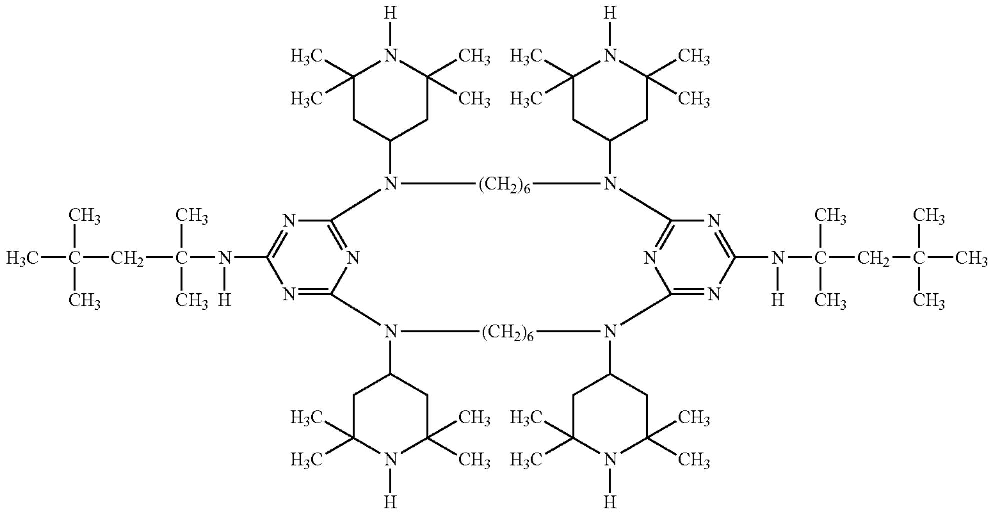

80-a)

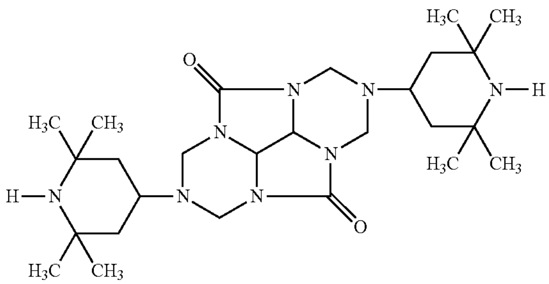

In the following compounds (81) to (83), (84-1), (84-2) and (85) to (91), (91-1), (92-1), (92-2), (93) and (94), $m_1$ to $m_{14}$ is a number from 2 to about 200, preferably 2 to 100, for example 2 to 50, 2 to 40 or 3 to 40 or 4 to 10.

81)

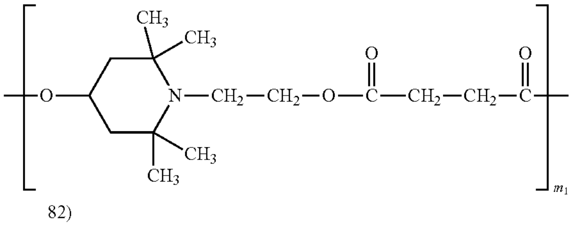

82)

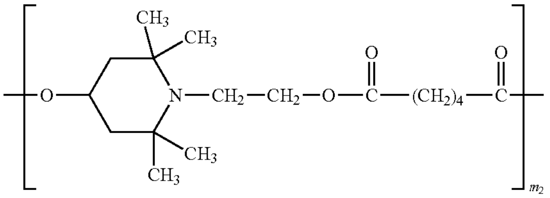

In the compounds (81) and (82), the end group bonded to the —O— can be, for example, hydrogen or a group —CO—$(CH_2)_2$—COO—Y or —CO—$(CH_2)_4$—COO—Y, respectively, with Y being hydrogen or $C_1$-$C_4$alkyl and the end group bonded to the diacyl can be, for example, —O—Y or a group

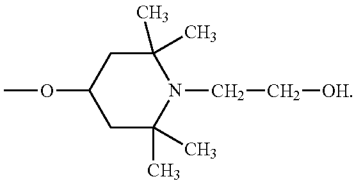

83)

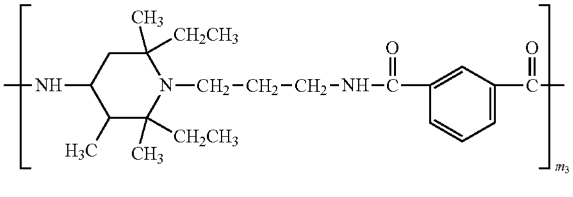

In the compound (83), the end group bonded to the amino residue can be, for example, a group

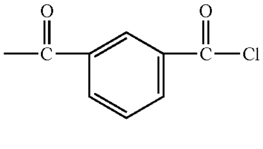

and the end group bonded to the diacyl residue can be, for example, Cl.

84-1)

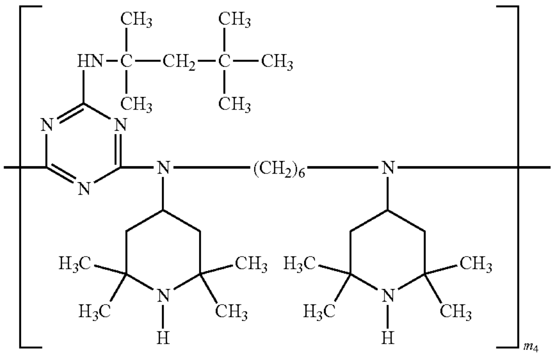

84-2)

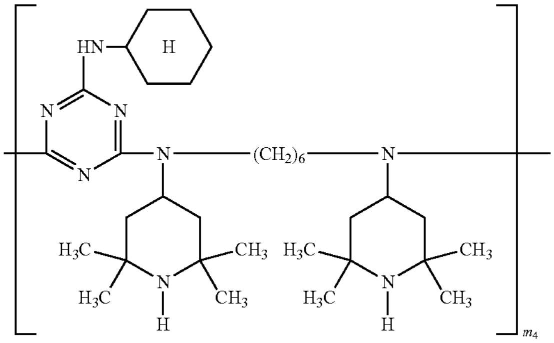

In the compounds (84-1) and (84-2), the end group bonded to the triazine residue can be, for example, chlorine or a group

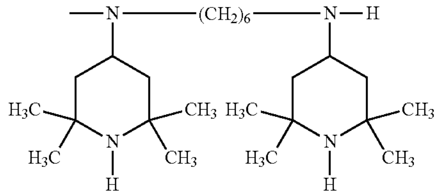

and the end group bonded to the diamino group can be, for example, hydrogen or a group

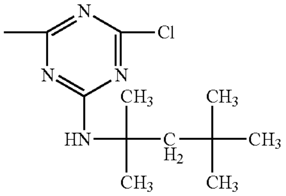

or

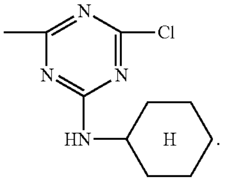

It may be convenient to replace the chlorine attached to the triazine by e.g. —OH or an amino group. Suitable amino groups are typically: pyrrolidin-1-yl, morpholino, —$NH_2$, —$N(C_1$-$C_8$-alkyl$)_2$ and —NY'($C_1$-$C_8$-alkyl) wherein Y' is hydrogen or a group of the formula

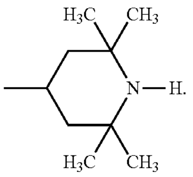

85)

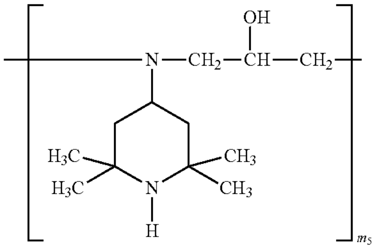

In the compound (85), the end group bonded to the 2,2,6,6-tetramethylpiperidin-4-ylamino residue can be, for example, hydrogen and the end group bonded to the 2-hydroxypropylene residue can be, for example,

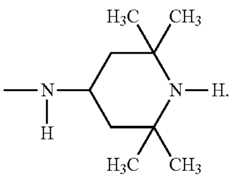

86)

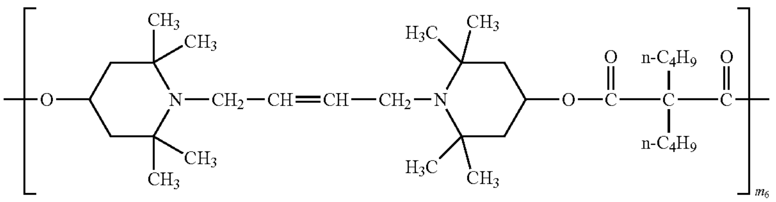

In the compound (86), the end group bonded to the —O— can be, for example, hydrogen or

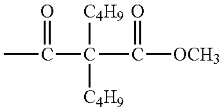

and the end group bonded to the diacyl residue can be, for example, —OCH3 or Cl.

87)

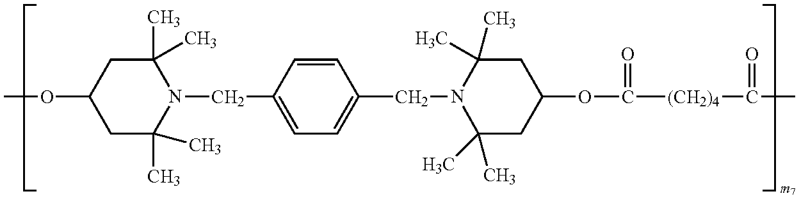

In the compound (87), the end group bonded to the —O— can be, for example, hydrogen or

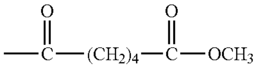

and the end group bonded to the diacyl radical can be, for example, —OCH3 or Cl.

88)

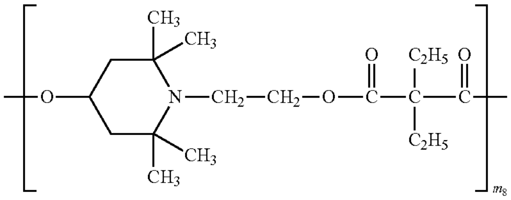

In the compound (88), the end group bonded to the —O— can be, for example, hydrogen or

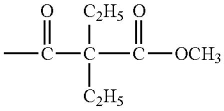

and the end group bonded to the diacyl radical can be, for example, —OCH3 or Cl.

89)

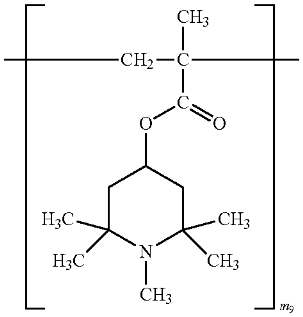

In the compound (89), the end group bonded to the —CH2- can be, for example, hydrogen and the end group bonded to the ester residue can be, for example,

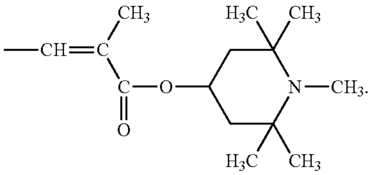

90)

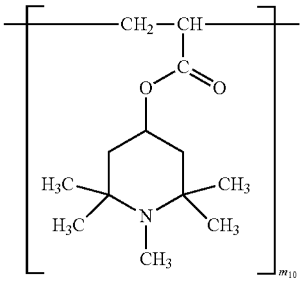

In the compound (90), the end group bonded to the —CH2- can be, for example, hydrogen and the end group bonded to the ester residue can be, for example,

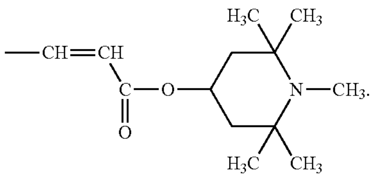

91)

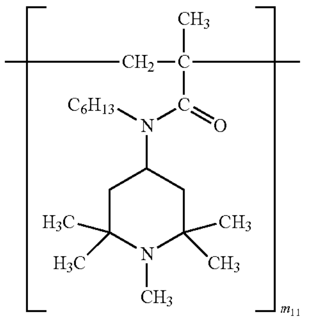

In the compound (91), the end group bonded to the —$CH_2$— can be, for example, hydrogen and the end group bonded to the amide residue can be, for example,

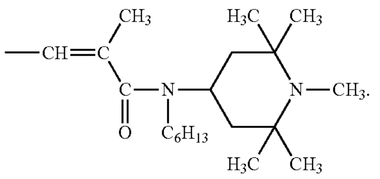

91-1)

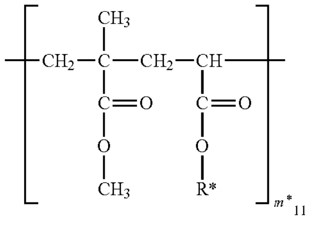

wherein $m_{11}$* is as defined for $m_{11}$, the radicals R* independently of one another are ethyl or 2,2,6,6-tetramethylpiperidin-4-yl, with the proviso that at least 50% of the radicals R* are 2,2,6,6-tetramethylpiperidin-4-yl and the remaining radicals R* are ethyl. In the compound (91-1), the terminal groups are for example hydrogen.

92-1)

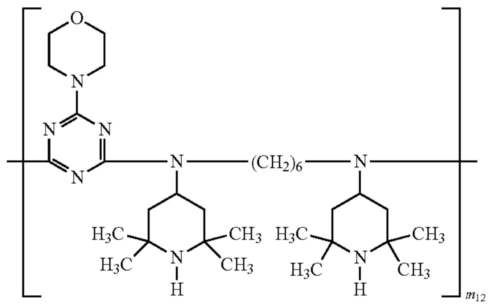

(CA-RN 90751-07-8)

92-2)

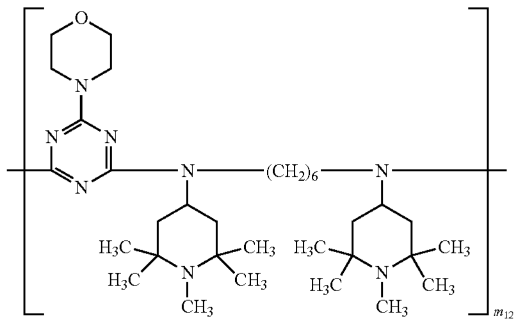

(CA-RN219920-30-6)

In the compounds (92-1) and (92-2), the end group bonded to the triazine residue can be, for example, chlorine or a group

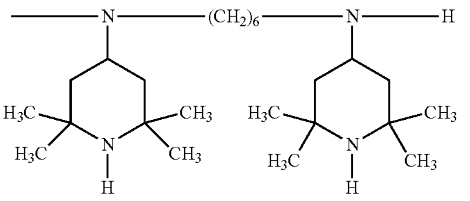

in the compound (92-1), and a group

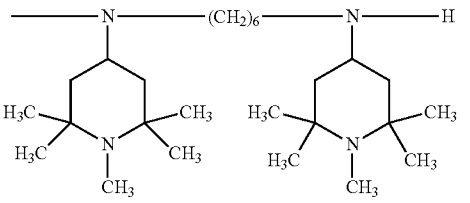

in the compound (92-2), and the end group bonded to the diamino residue can be, for example, hydrogen or a group

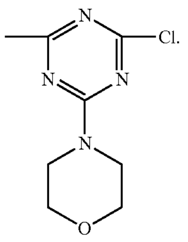

It may be convenient to replace the chlorine attached to the triazine by e.g. —OH or an amino group. Suitable amino groups are typically: pyrrolidin-1-yl, morpholino, $—NH_2$, $—N(C_1\text{-}C_8\text{-alkyl})_2$ and $—NY'(C_1\text{-}C_8\text{-alkyl})$ wherein Y' is hydrogen or a group of the formula

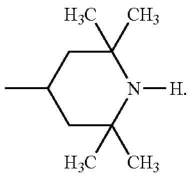

93)

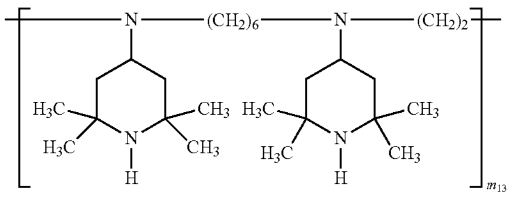

In the compound (93), the end group bonded to the diamino residue can be, for example, hydrogen and the end group bonded to the —CH2CH2- residue can be, for example,

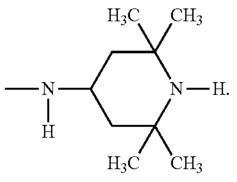

94)

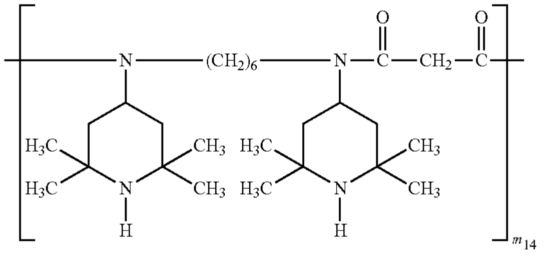

In the compound (94), the end group bonded to the diamino residue can be, for example, hydrogen and the end group bonded to the diacyl residue can be, for example, Cl.

95)

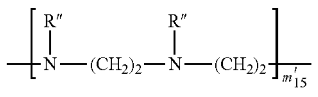

in which R" is a group of the formula (95-I)

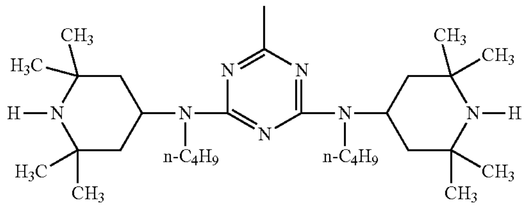

or the chain branching

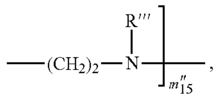

R''' is a group of the formula (95-I), and m'15 and m"15 are each a number from 0 to 200, preferably 0 to 100, in particular 0 to 50, with the proviso that m'15+m"15 is a number from 2 to 200, preferably 2 to 100, in particular 2 to 50. In the compound 95, the end group bonded to the diamino residue can be, for example, hydrogen and the end group bonded to the $—CH_2CH_2—$ group can be, for example, halogen, in particular Cl or Br.

96) the compound of the formula (96-I) or (96-II)

(96-I)

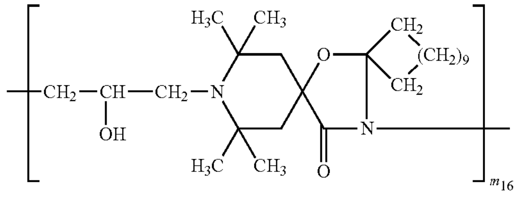

(96-II)

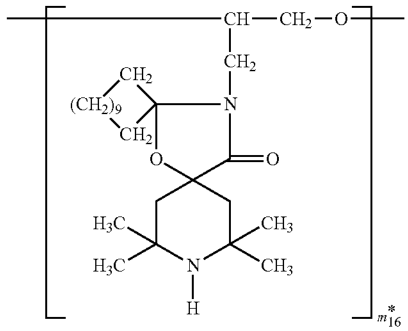

wherein m16 and m16* are a number from 2 to 50.

During the preparation, the compounds of the formulae (96-I) and (96-II) can be obtained together as a mixture and therefore, can also be employed as such. The (96-I):(96-II) ratio is, for example, from 20:1 to 1:20 or from 1:10 to 10:1.

In the compounds of the formula (96-I), the terminal group bonded to the nitrogen can be, for example, hydrogen and the terminal group bonded to the 2-hydroxypropylene radical can be, for example, a

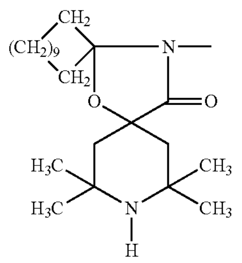

group.

In the compounds of the formula (96-II), the terminal group bonded to the dimethylene radical can be, for example, —OH, and the terminal group bonded to the oxygen can be, for example, hydrogen. The terminal groups can also be polyether radicals.

96-a)

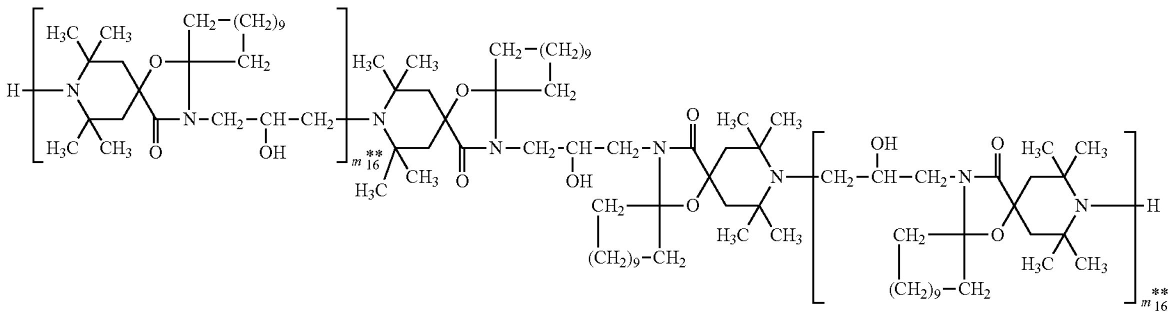

wherein the variables m16** are independently of one another as defined for m16.

97-1)

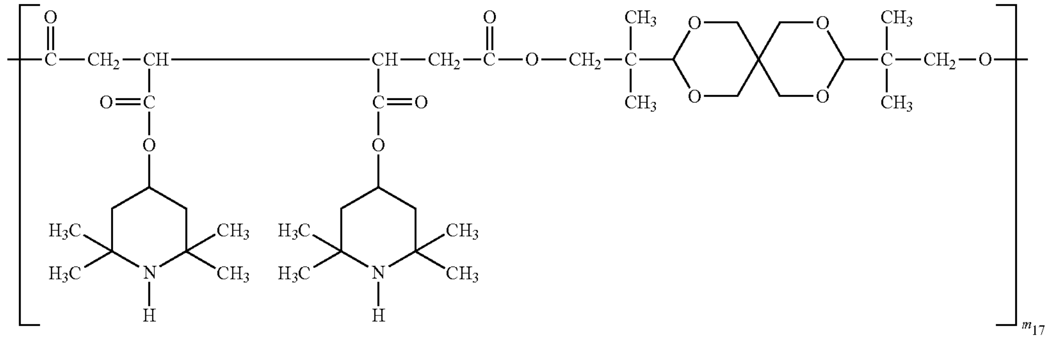

-continued 97-2)

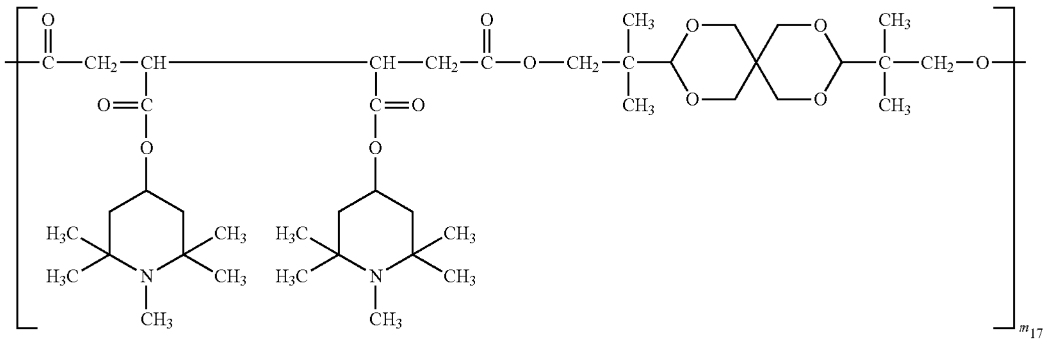

In the compounds (97-1) and (97-2) the mean value of m17 is 2.5 and the end group bonded to the >C═O group can be, for example,

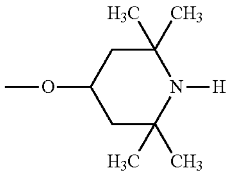

in the compound (97-1) and

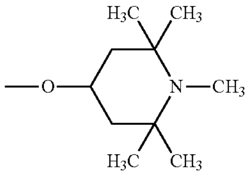

in the compound 97-2); and the end group bonded to the oxygen can be, for example

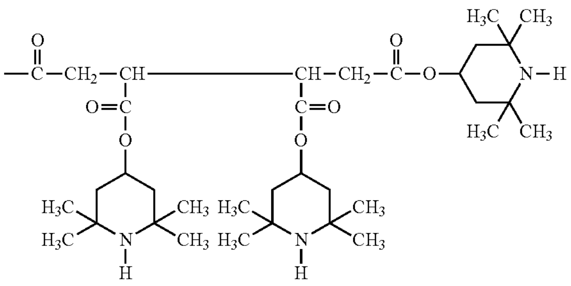 [SMILES: CC(=O)CC(C(=O)OC1CC(C)(C)NC(C)(C)C1)C(CC(=O)OC1CC(C)(C)NC(C)(C)C1)C(=O)OC1CC(C)(C)NC(C)(C)C1]

in compound (97-1) and

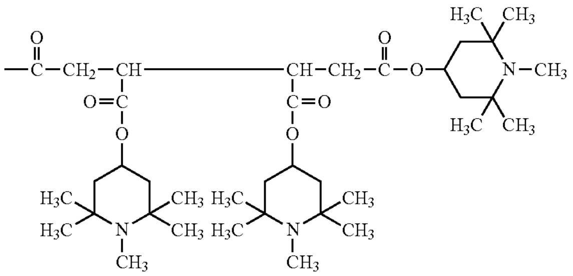 [SMILES: CC(=O)CC(C(=O)OC1CC(C)(C)N(C)C(C)(C)C1)C(CC(=O)OC1CC(C)(C)N(C)C(C)(C)C1)C(=O)OC1CC(C)(C)N(C)C(C)(C)C1]

in compound 97-2).

98)

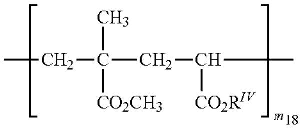

wherein approximately one third of the radicals RIV are —C2H5 and the others are a group

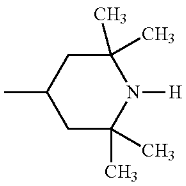

and $m_{18}$ is a number in the range from 2 to 200, preferably 2 to 100, in particular 2 to 50.

In the compound (98), the end group bonded to the —$CH_2$— residue can be, for example, hydrogen and the end group bonded to the —$CH(CO_2R^{IV})$— residue can be, for example, —CH═CH—$COOR^{IV}$.

99-1)

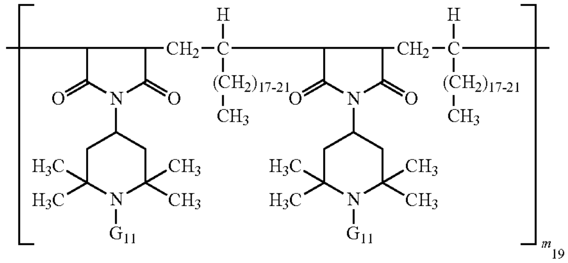

99-2)

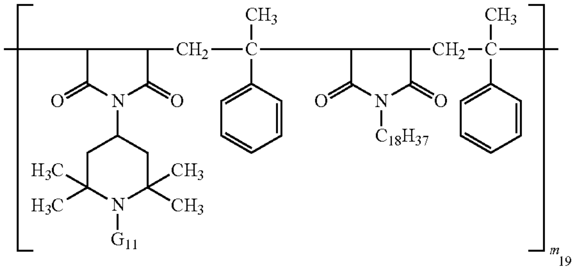

99-3)

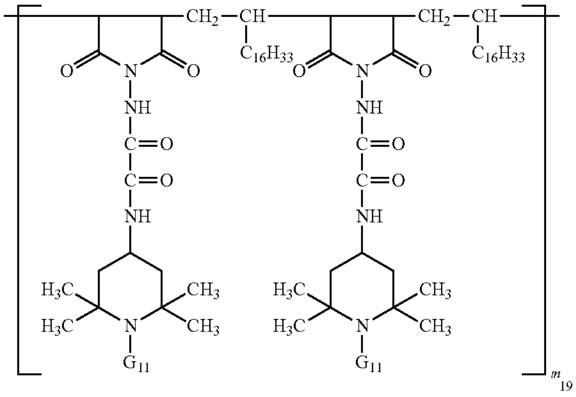

In the compounds (99-1), (99-2) and (99-3), G11 is hydrogen or methyl, and m19 is a number from 1 to 25.

In the compounds (99-1), (99-2) or (99-3), the end group bonded to the 2,5-dioxopyrrolidine ring can be, for example, hydrogen, and the other end group can be, for example, a group of the formula

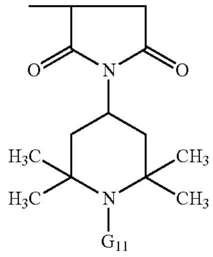

in the compounds (99-1) and (99-2), and a group of the formula

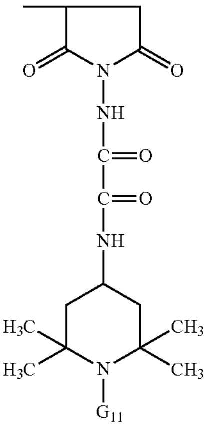

in compound (99-3).

100) A product obtainable by reacting a product, obtained by reaction of a polyamine of the formula (100a) with cyanuric chloride, with a compound of the formula (100b)

(100a)

$$H_2N-(CH_2)_{m'_{20}}-NH-(CH_2)_{m''_{20}}-NH-(CH_2)_{m'''_{20}}-NH_2$$

(100b)

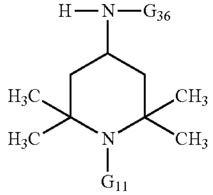

in which $m'_{20}$, $m''_{20}$ and $m'''_{20}$, independently of one another, are a number from 2 to 12, $G_{36}$ is hydrogen, $C_1$-$C_{12}$alkyl, $C_5$-$C_{12}$cycloalkyl, phenyl or $C_7$-$C_9$phenylalkyl, and $G_{11}$ is hydrogen or methyl. The product with $G_{11}$ being hydrogen has the Chemical Abstracts-CAS No. 136 504-96-6.

In general, the above reaction product can be represented for example by a compound of the formula (100-1), (100-2) or (100-3). It can also be in the form of a mixture of these three compounds.

(100-1)
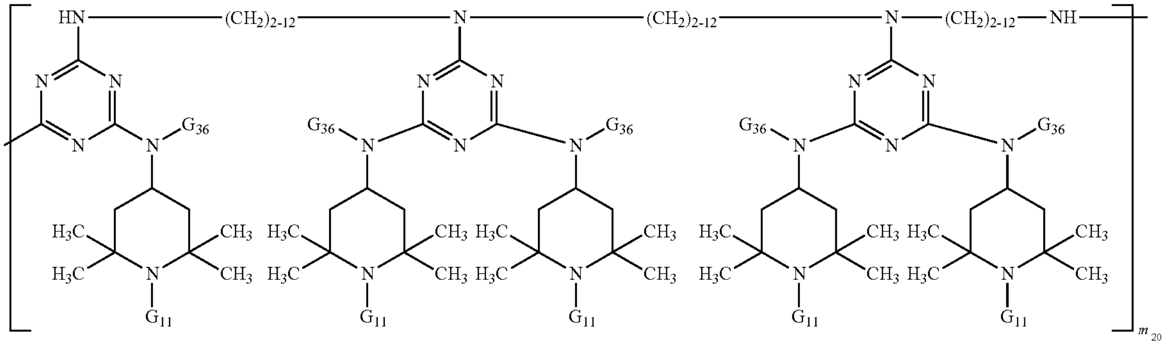
(100-2)
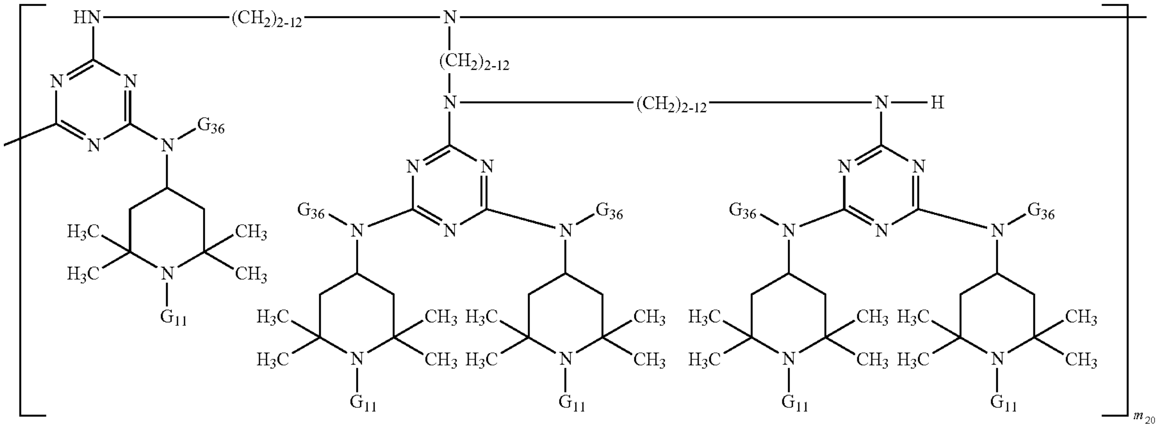
(100-3)
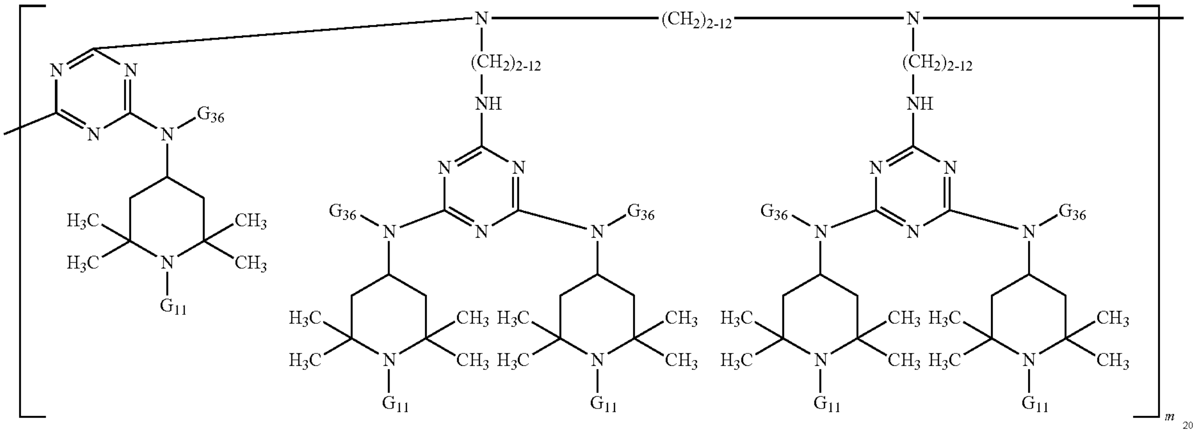

A preferred meaning of the formula (100-1) is
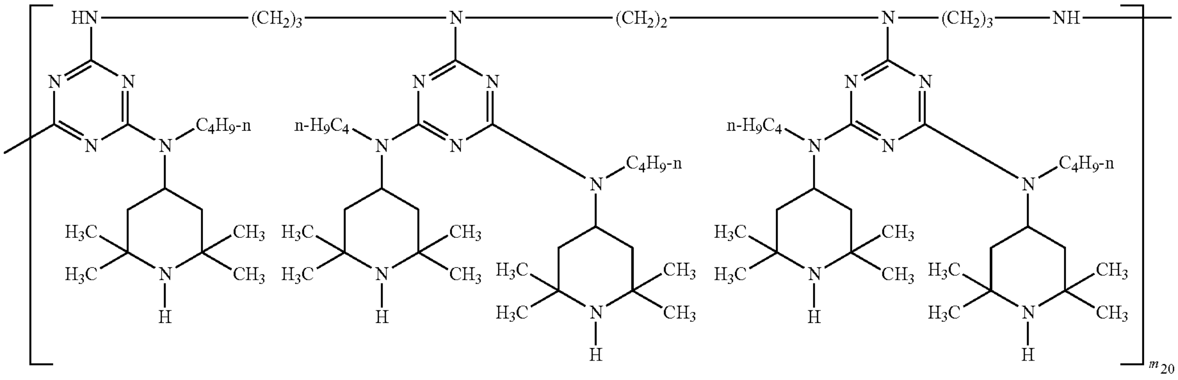
A preferred meaning of the formula (100-2) is
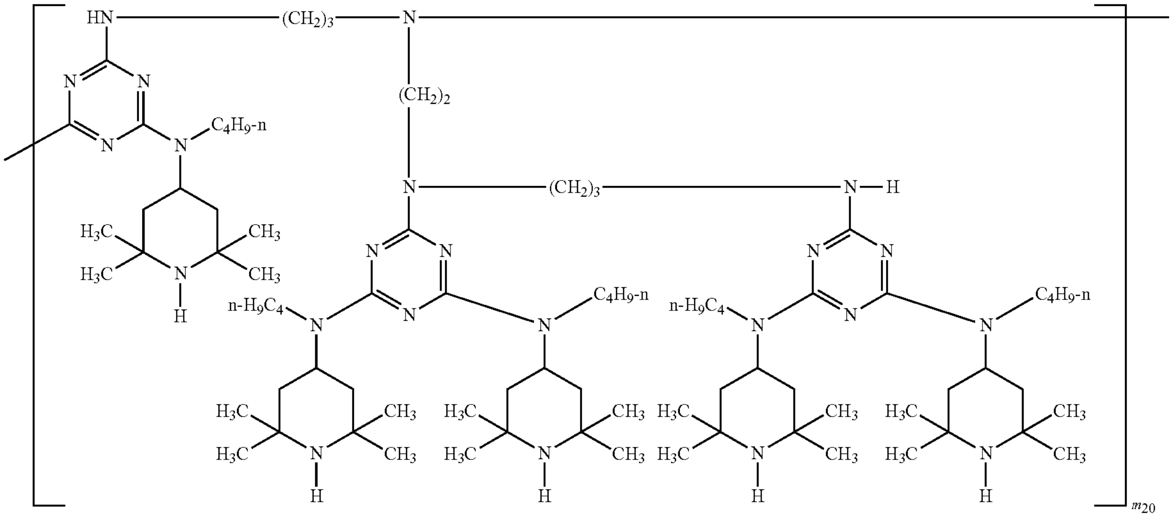
A preferred meaning of the formula (100-3) is
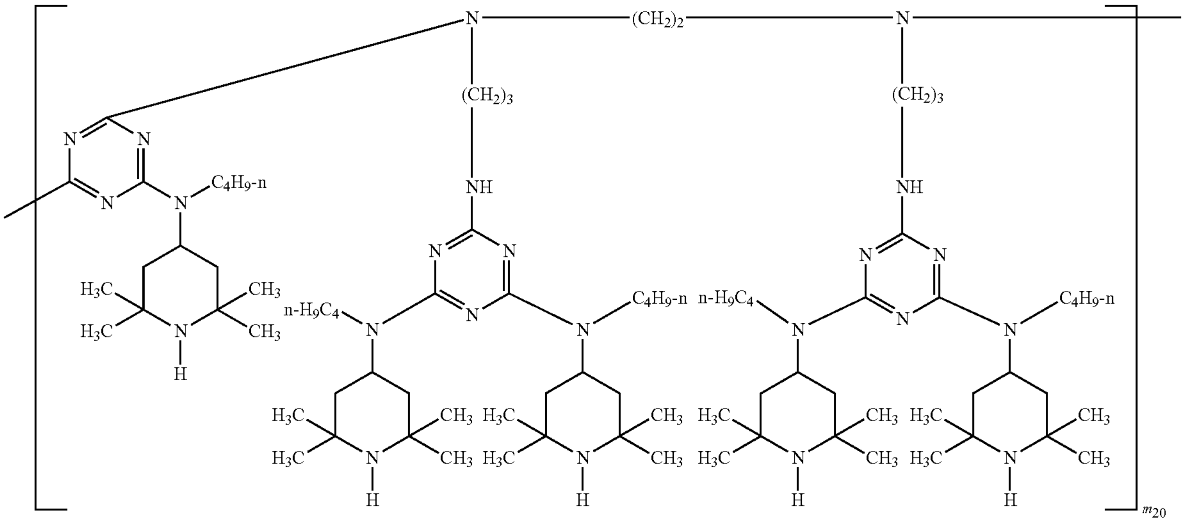

In the above formulae (100-1) to (100-3), m20 is e.g. 1 to 20, preferably 2 to 20.

101)

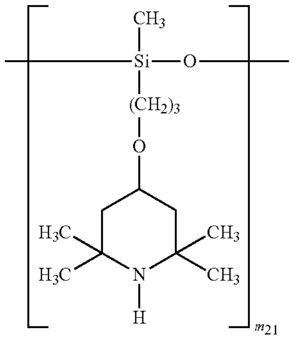

with $m_{21}$ being a number from 1 to 20.

In the compound (101), the terminal group bonded to the silicon atom can be, for example, $(CH_3)_3Si—O—$, and the terminal group bonded to the oxygen can be, for example, $—Si(CH_3)_3$. The compounds (101) can also be in the form of cyclic compounds if $m_{21}$ is a number from 3 to 10, i.e. the free valences shown in the structural formula then form a direct bond.

102)

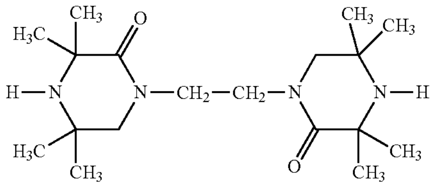

103)

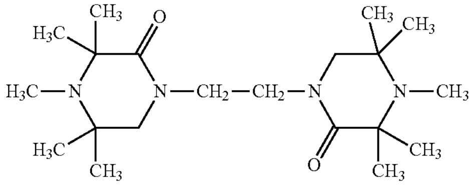

104)

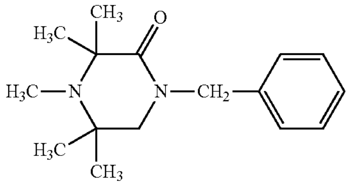

105)

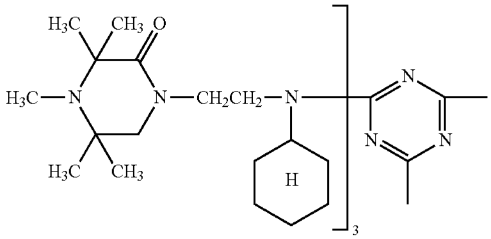

-continued
106)
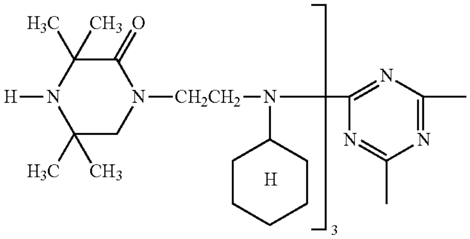
107)
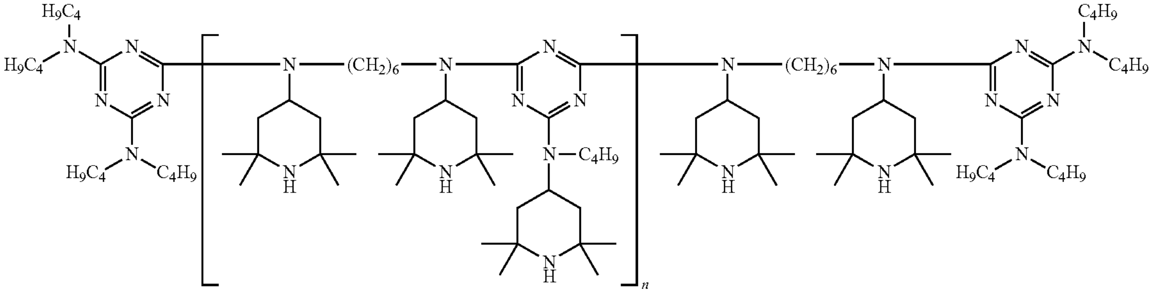
108)
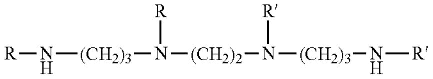
where R is
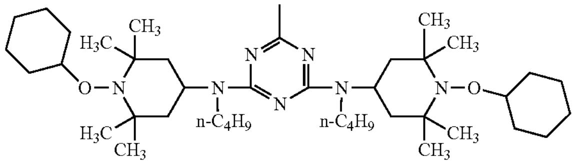
and one of the residues R' is R and the other is H;
109)
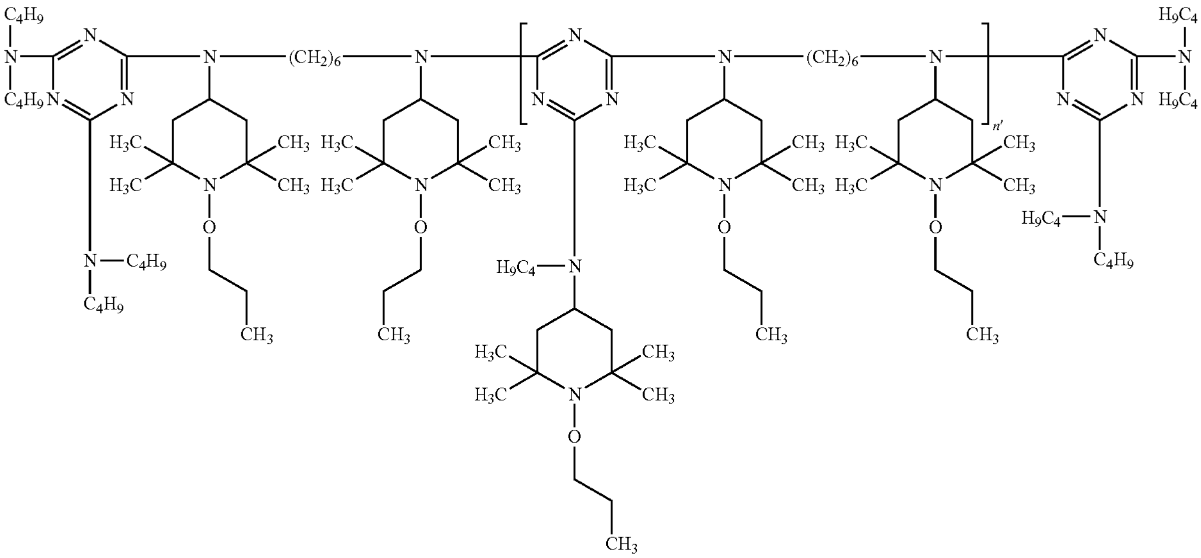

110) 5-(2-ethylhexanoyl)oxymethyl-3,3,5-trimethyl-2-morpholinone as disclosed in example A19 of U.S. Pat. No. 6,140,326;

111)

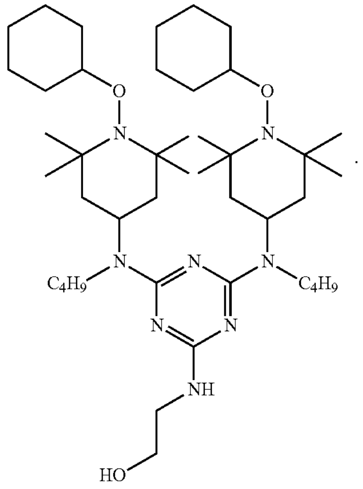

The sterically hindered amine of the above section can also be one of the compounds described in GB-A2,301,106 as component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 14-1, 1-g-1, 1-g-2 or 1-k-1 listed on pages 68 to 73 of said GB-A-2,301,106.

The sterically hindered amine of the above section may also be one of the compounds described in EP 782994, for example compounds as described in claim 10 or 38 or in Examples 1-12 or D-1 to D-5 therein.

Furthermore useful are sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethyl-piperidine, bis(1-(2-hydroxy-2-methylpropoxy)-2,2,6,6-tetramethyl-piperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxyethylamino)-s-triazine.

112) 1-(2-hydroxy-2-methylpropoxy)-4-octadecanoyloxy-2,2,6,6-tetramethylpiperidine of formula

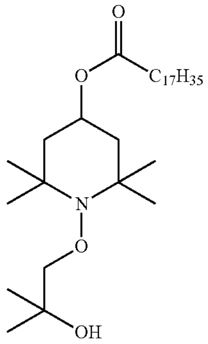

Preferred HALS compounds are compounds 13, 14a, 24, 76, 81, 84-1, 92-1, 92-2, 107, 108, 109, 110 and/or 112.

Furthermore preferred HALS compounds 2,2,6,6-tetramethyl-4-piperidon; 2,2,6,6-tetramethyl-4-piperidinol; bis-(1,22,6,6-pentamethylpiperidyl)-(3',5'-di-tert-butyl-4'-hydroxy-benzyl)-butylmalonate; bis-(2,2,6,6-tetramethyl-4-piperidinyl)-decanedioate (Tinuvin® 770); bis-(2,2,6,6-tetramethyl-4-piperidinyl)-succinate (Tinuvin® 780); bis-(1-octyloxy-2,2,6,6-tetramethyl-4-piperidinyl)-sebacate (Tinuvin® 123); bis-(1,2,2,6,6-pentamethyl-4-piperidinyl)-sebacate (Tinuvin® 765); tetrakis-(2,2,6,6-tetramethyl-4-piperidyl)-1,2,3,4-butane-tetracarboxylaat; N,N'-bis-(2,2,6,6-tetramethyl-4-piperidyl)-hexane-1,6-diamine; N-butyl-2,2,6,6-tetramethyl-4-piperidinamine; 5-(2,2,6,6-tetramethyl-4-piperidinyl)-2-cyclo-undecyl-oxazole) (Hostavin® N20); 1,1-(1,2-ethane-di-yl)-bis-(3,3',5,5'-tetramethylpiperazinone) (Goodrite® UV3034); 8-acetyl-3-dodecyl-7,7,9,9-tetramethyl-1,3,8-triazaspiro(4,5)decaan-2,4-dione (Tinuvin® 440); 1,2,3,4-butane-tetracarboxylic acid-1,2,3-tris(1,2,2,6,6-pentamethyl-4-piperidinyl)-4-tridecylester (Mark® LA62); N-2,2,6,6-tetrametyl-4-piperidinyl-N-amino-oxamide (Luchem® HAR100); 4-acryloyloxy-1,2,2,6,6-pentamethyl-4-piperidine; Mixture of esters from 2,2,6,6-tetramethyl-4-piperidinol and fatty acids (Cyasorb® UV3853); Propanedioic acid, [(4-methoxyphenyl)methylene]-,bis(1,2,2,6,6-pentamethyl-4-piperidinyl) ester (Sanduvor® PR 31); Formamide, N,N'-1,6-hexanediylbis[N-(2,2,6,6-tetramethyl-4-piperidinyl (Uvinul® 4050H); 1,5-Dioxaspiro (5,5) undecane 3,3-dicarboxylic acid, bis(2,2,6,6-tetramethyl-4-peridinyl) ester (Cyasorb® UV-500); 1,5-Dioxaspiro (5,5) undecane 3,3-dicarboxylic acid, bis(1,2,2,6,6-pentamethyl-4-peridinyl) ester (Cyasorb® UV516); 3-dodecyl-1-(2,2,6,6-tetramethyl-4-piperidyl)-pyrrolidin-2,5-dione (Cyasorb® UV3581) 3-dodecyl-1-(1,2,2,6,6-pentamethyl-4-piperidyl)-pyrrolidin-2,5-dione.

The compounds useful as antioxidants or UV-stabilizer according to the present invention optionally in combination with a hindered amine light stabilizer and optional further stabilizers may be added to the organic material to be stabilized, e.g. the thermoplastic polymer, preferably the polyolefin, individually or mixed with one another. If desired, the individual components of such a stabilizer mixture can be mixed with one another in the melt (melt blending) before incorporation into the organic material to be stabilized.

The incorporation of the additives of the invention and optional further components into the thermoplastic polymer is carried out by known methods such as dry blending in the form of a powder, or wet mixing in the form of solutions, dispersions or suspensions for example in an inert solvent, water or oil. The additives of the invention and optional further additives may be incorporated, for example, before or after moulding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twinscrew extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion*, Vol. 1 Grundlagen, Editors F. Hensen, W. Knappe, H. Potente, 1989, pp. 3-7, ISBN:3-446-14339-4 (Vol. 2 *Extrusionsanlagen* 1986, ISBN 3-446-14329-7).

For example, the screw length is 1-60 screw diameters, preferably 35-48 screw diameters. The rotational speed of the screw is preferably 10-600 rotations per minute (rpm), very particularly preferably 25-300 rpm.

The maximum throughput is dependent on the screw diameter, the rotational speed and the driving force.

The process of the present invention can also be carried out at a level lower than maximum throughput by varying the parameters mentioned or employing weighing machines delivering dosage amounts.

If a plurality of components is added, these can be premixed or added individually.

The additives of the invention and optional further additives can also be added to the polymer in the form of a masterbatch ("concentrate") which contains the components in a concentration of, for example, about 1% to about 40% and preferably 2% to about 20% by weight incorporated in a polymer. The polymer need not be necessarily of identical structure than the polymer where the additives are added finally. In such operations, the polymer can be used in the form of powder, granules, solutions, suspensions or in the form of latices.

Incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the additives of the invention into polymers is to add them before, during or directly after the polymerization of the corresponding monomers or prior to crosslinking. In this context the additive of the invention can be added as it is or else in encapsulated form (for example in waxes, oils or polymers).

The materials containing the additives of the invention described herein can be used for the production of mouldings, rotomoulded articles, injection moulded articles, blow moulded articles, pipes, films, tapes, mono-filaments, fibers, nonwovens, profiles, adhesives or putties, surface coatings and the like.

The stabilizers according to the invention and optional further stabilizers are preferably present in the material to be stabilized in an amount of 0.01 to 10% by weight, relative to the material to be stabilized. An amount of 0.01 to 5% by weight or 0.05 to 2% by weight, in particular 0.05 to 0.5% by weight is especially preferred.

The stabilizer(s) according to the invention and optional further additives can also be added to the material to be stabilized in the form of a masterbatch which contains these components in a concentration of, for example, about 2.5% to about 25% by weight; in such operations, the polymer can be used in the form of powder, granules, solutions, suspensions or in the form of latices.

Where sterically hindered amines (HALS) are present, these are preferably used in a ratio of HALS:Antioxidant ranging from 1:10 to 20:1, especially from 1:3 to 10:1.

Methods:

Oxygen Induction Time (OIT)—Variant 1 (Used in Example 3)

The OIT test was performed after storage for 4 days at room temperature under exclusion of light according to ISO 11357-6:2008 using a Differential Scanning calorimeter (DSC). A round sample, punched out from a compression moulded plate prepared according to ISO 1873-2, having a diameter of 5 mm and a weight of 15 mg of the material to be tested is introduced into the DSC at room temperature, and the sample is heated to 220° C. under a nitrogen atmosphere (20 ml nitrogen/min) with 20° C./min. As soon as 220° C. is reached the cell is maintained in an isothermal condition, and the gas is changed from nitrogen to oxygen. The flow rate of the oxygen is maintained at 20 ml/min. Under these conditions the stabilizer is consumed over time until it is totally depleted. At this point the polymer sample degrades or oxidizes liberating additional heat (exothermal reaction).

The time (in minutes) it takes for this exotherm reaction to appear from the time that the oxygen is introduced is reported as the OIT time, and is a measure of the oxidation stability of the material.

Oxygen Induction Time (OIT)|Variant 2 (Used in Example 8)

The OIT test was performed after storage for 4 days at room temperature under exclusion of light according to ISO 11357-6:2008 using a Differential Scanning calorimeter (DSC). A round sample, punched out from a compression moulded plate prepared according to ISO 1873-2, having a diameter of 5 mm and a weight of 10 mg of the material to be tested is introduced into the DSC at room temperature, and the sample is heated to 210° C. under a nitrogen atmosphere (50 ml nitrogen/min) with 20° C./min. As soon as 210° C. is reached the cell is maintained in an isothermal condition for 5 minutes, and the gas is changed from nitrogen to oxygen. The flow rate of the oxygen is maintained at 50 ml/min. Under these conditions the stabilizer is consumed over time until it is totally depleted. At this point the polymer sample degrades or oxidizes liberating additional heat (exothermal reaction). The time (in minutes) it takes for this exothermal reaction to appear from the time that the oxygen is introduced is reported as the OIT time, and is a measure of the oxidation stability of the material.

Calculation: (Same for Variant 1 and 2)

The data is plotted with the heat-flow signal (mW) on the y-axis, versus time on the x-axis. The x-axis should be expanded as much as possible to facilitate analysis.

The oxidation induction time, is the time calculated in minutes, from the introduction of oxygen to the intercept of the extended baseline and the extended tangent, drawn to the exothermic at the point of maximum slope.

Double samples are measured, and the mean value is calculated.

Multiple Extrusion:

The desired amount of antioxidant, acid scavenger and polypropylene homopolymer powder were premixed in an intensive mixer, and the multiple-extrusion was done on a Coperion ZSK 18 twin screw extruder with a length/diameter (L/D) ratio of 40. The through put and the speed of the screw were fixed at 7.5 kg/h and 300 rpm, respectively. For the first extrusion, the temperature profile was 190-200-210-220-230-230-230° C., from the main hopper to die, and the melt temperature was 230° C. From the second to the fifth extrusion, the temperature profile was changed to 200-210-220-230-250-250-250° C., with a melt temperature of 250° C.

MFR after Each Extrusion Cycle:

The melt flow rate (MFR) of the polypropylene after multiple extrusion was measured as the MFR2 in accordance with ISO 1133 (230° C., 2.16 kg load), and is indicated in g/10 min. The MFR is an indication of the flowability. The higher the melt flow rate, the lower the viscosity of the polymer.

Rheomix 540 OS (Example 8)

Compounding of antioxidant with neat PP and Ca-stearate in a Rheomix 540 OS:

Neat PP powder from Borealis (HD 120) was mixed with Ca-Stearate and different amounts of antioxidants according to the invention as well as two commercial antioxidant types (Irganox 1010, Irganox 3114) as reference in a Thermo Haake Rheomix 540 OS at 230° C. for 3 minutes. The material out of the kneader was crushed to prepare for further use (pressing of test samples for rheological measurements in Example 8 or measuring the oxygen induction time (OIT) in Example 8).

Pressing of Test Samples for Rheology Measurements:

The crushed material from the kneading process was transferred in a preheated mould of 200° C. After cooling of the mould test specimens—PP resin pallets—could be obtained.

RheoStress 600 Rheometer

Determination of rheological properties of the compounds was done by using a RheoStress 600, a rheometer from Company ThermoHaake. The measurements were performed at 250° C., with a constant frequency of 1 Hz so that G' is in the linear range. Decreasing of the viscosity was measured over time so that the aging of the PP was visible.

Mode: Timesweep—Oscillation
frequency=1 Hz
shear stress=2000 Pa
temperature=250° C.
time=3600 sec
gap=0.5 mm Analytical Data were Measured with:

DSC System: Perkin Elmer DSC 8000 (used in Example 2)
TGA System: Perkin Elmer TGA 4000 (used in Example 2)
DSC/TGA System: Netzsch 449C/1/G Jupiter (used in Examples 4 to 7)
DSC System for OIT Test: Netzsch DSC 204 HP Phoenix (used in Examples 4 to 7)

HPLC System:

Thermo Electron Corporation, Finnigan Surveyor with MS Pump Plus, Autosampler Plus, PDA Plus Detector with Thermo Finnigan, LCQ DECA XP$^{plus}$ mass detection (used in Example 2)

Agilent 1260 Infinity, DAD Detector 1260 G42128, MS: APCI-ES G19488, QQQ MS 6420 G6420A (used in Examples 4 to 7)

NMR Spectrometer:

Bruker, Avance DPX 200 NMR spectrometer (200 MHz) (used in Example 2)

Bruker Advance III 400 NMR spectrometer (used in Examples 4 to 7)

In Examples 4 to 7 all NMR spectroscopy was recorded in the solution-state using a Bruker Advance III 400 NMR spectrometer operating at 400.15 and 100.62 MHz for 1H and 13C respectively. All spectra were recorded using a 5 mm inverse (BBO) probehead at 30° C. using nitrogen gas for all pneumatics. For 1H standard single-pulse excitation was employed with a 30 degree tip angle collecting 16 transients. For 13C {1H} measurements single pulse excitation with NOE and WALTZ16 decoupling was used collecting 1024 (1k) transients.

IR: Bruker Tensor 27 (used in Examples 4 to 7)

Elementar Analysis: Elementar vario Max CHN (used in Examples 4 to 7)

EXAMPLES

Example 1

Synthesis of (1,3,5-triazine-2,4,6-triyl)tris(methylazanediyl)trimethanol ($C_9H_{18}N_6O_3$)

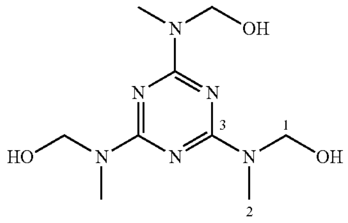 [SMILES: CN(CO)c1nc(N(C)CO)nc(N(C)CO)n1]

2,4,6-Tris[(hydroxymethyl)methylamino]-1,3,5-triazine, Trimelamol

In a 2000 $cm^3$ three-necked round bottom flask connected to a condenser and fitted with a thermometer 150.2 g (0.893 mol) 2,4,6-tris(methylamino)-1,3,5-triazine and 17.1 g (0.124 mol) potassium carbonate were suspended in 520 $cm^3$ water. During 15 minutes and efficient stirring 233.0 $cm^3$ (2.95 mol) aqueous formaldehyde solution (35%) were added to the suspension at ambient temperature. The reaction mixture was then rapidly heated to 70° C. and stirred at temperature for further 20 minutes. During the heating period the suspension turned into a colourless solution. After the heating period the reaction solution was allowed to cool to room temperature, followed by stirring over night, for 12 hours. The precipitate was filtered, washed three times with cold water (each 200 $cm^3$) and dried at 40° C. in a drying cabinet yielded 196.4 g (85%) as white solid. No further purification was necessary.

Mp.: 129-131° C.

$^1H$ NMR (200 MHz, DMSO-d6, 30° C.): δ=5.42 (t, J=7.0 Hz, 1H, OH), 4.98 (d, J=7.0 Hz, 2H, H1), 3.02 (s, 3H, H2) ppm $^{13}C$ NMR (50 MHz, DMSO-d6, 30° C.): δ=165.1 (C3), 70.72 (C1), 32.50 (C2) ppm FT-IR (KBr, v): 3391, 3265, 2943, 1558, 1503, 1394, 1323, 1280, 1245, 1225, 1156, 1024, 998, 862, 811, 739, 690, 623, 589 $cm^{-1}$ Example 2

Synthesis of 4,4',4"-(((1,3,5-triazine-2,4,6-triyl)tris (methylazanediyl))tris(methylene))-tris(2,6-di-tert-butylphenol) (Structure 6; $C_{51}H_{78}N_6O_3$)

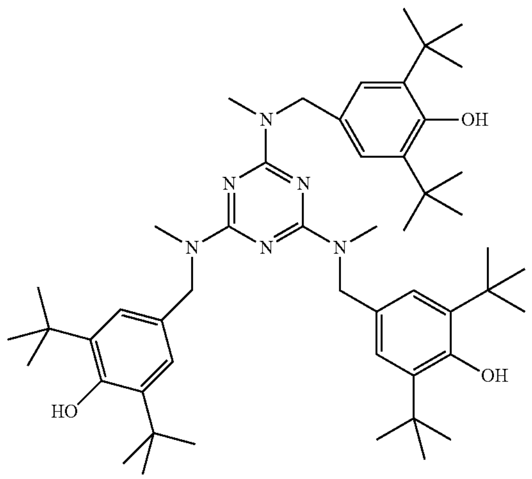 [SMILES: CN(Cc1cc(C(C)(C)C)c(O)c(C(C)(C)C)c1)c1nc(N(C)Cc2cc(C(C)(C)C)c(O)c(C(C)(C)C)c2)nc(N(C)Cc2cc(C(C)(C)C)c(O)c(C(C)(C)C)c2)n1]

In a 100 $cm^3$ three-necked round bottom flask, equipped with a thermometer and a condenser, 12.53 g (60.7 mmol) 2,6-Di-tert-butyl phenol were dissolved in 20 $cm^3$ acetonitrile. Then, 2.4 $cm^3$ (30.3 mmol) aqueous formaldehyde solution (35%) were added, the reaction mixture was intensively mixed, followed by the addition of 2.53 g (9.85 mmol) 2,4,6-tris[(hydroxyl-methyl)methylamino]-1,3,5-triazine, prepared as described in Example 1. Adjacent, 15.0 $cm^3$ (390 mmol) formic acid (98%) were added rapidly and the mixture was stirred in an 80° C. pre-tempered oil bath for seven hours. Evaporation of the reaction medium afforded the crude product as a yellow high viscous mass containing 6 greater than 85%.

Mp.: 185° C. (DSC, 10° C.·$min^{-1}$)

$^1H$ NMR (200 MHz, $CDCl_3$, 30° C.): δ=7.17 (s, 2H, Ar—H), 5.09 (s, 1H, —OH), 4.76 (s, 2H, —$CH_2$—), 3.10 (s, 3H, N—$CH_3$), 1.42 (s, 18H, —$C(CH_3)_3$) ppm $^{13}C$ NMR (50 MHz, $CDCl_3$, 30° C.): δ=166.2 (C7), 152.9 (C1), 135.9 (C2), 130.1 (C4), 125.2 (C3), 51.93 (C5), 34.54 (C8), 33.80 (C6), 30.57 (C9) ppm FT-IR (ATR): v=3641, 3597, 2954, 2913, 2870, 1531, 1500, 1485, 1429, 1390, 1360, 1309, 1270, 1231, 1208, 1149, 1120, 1044, 994, 965, 956, 931, 902, 885, 847, 809, 785, 770, 742, 705, 670, 648, 611, 590, 574, 562, 543, 531, 526 $cm^{-1}$ Isolation:

Crystallization from Acetone.

The raw product was dissolved in acetone and the solution was allowed to stand at room temperature without cover. The separated precipitate was filtered (sintered glass suction strainer, A2) and washed with small portions of cold 2-propanol or acetone to yield 6 as colourless crystals (purity: 99%+ from LC-MS peak areas of UV detection without response factor correction).

Example 3 a) The compound of Example 2 was added in an amount of 26.1 mg to 4.07 g neat polypropylene homopolymer powder, obtained by bulk polymerization using a Ziegler-Natta catalyst system ($MFR_2$ according to ISO 1133 0.2 g/10 min (230° C./2.16)

The composition was compounded in a Haake minilab Rheomex CTW5 screw compounder with the following conditions; 175° C.; 40 U/min, 5 min, 40 N/cm and 53 bar; and then processed into the test specimens as described under methods, Oxidation Induction Time Variant 1.

b) As Comparative Example CE1 the neat polypropylene powder as used in a) was processed into the OIT test specimens as described under methods, Oxidation Induction Time Variant 1.

c) As Comparative Example CE2 and CE3 test specimens from compounds with Irganox 3114 (25.4 mg into 4.0 g PP) and Irganox 1330 (25.4 mg into 4.0 g PP) were prepared as described for a).

The test results are shown in Table 1 and FIG. 1.

TABLE 1

| Example | OIT 220° C. |
|---|---|
| Example 3a) | 45 min |
| CE1 | 0.4 min |
| CE2 | 4 min |
| CE3 | 18 min |

From FIG. 1 and Table 1 it can be easily seen that the inventive use of the compound of Example 2 shows higher OIT times, thus being more effective than the commercially available antioxidants used.

Pure PP had an OIT-time of 0.4 min; PP compounded with Irganox 3114 had an OIT-time of 4 min; PP compounded with Irganox 1330 had an OIT-time of 18 min; whereas the PP compounded with the compound of Example 2 had an OIT-time of 45 min.

Example 4

Example 1 and 2 have been repeated to produce 4,4',4"-(((1,3,5-triazine-2,4,6-triyl)tris(methylazanediyl))tris(methylene))-tris(2,6-di-tert-butylphenol) (6; $C_{51}H_{78}N_6O_3$):

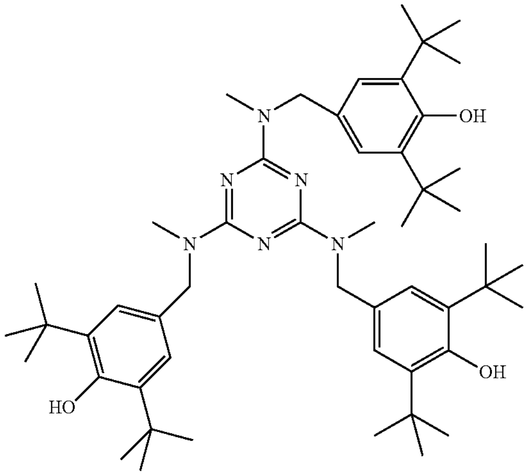 [SMILES: CN(Cc1cc(C(C)(C)C)c(O)c(C(C)(C)C)c1)c1nc(N(C)Cc2cc(C(C)(C)C)c(O)c(C(C)(C)C)c2)nc(N(C)Cc2cc(C(C)(C)C)c(O)c(C(C)(C)C)c2)n1]

Mp.: 188° C. (TGA/DSC)

Decomposition: 280° C.

purity: 98% from LC-MS peak areas of UV detection without response factor correction No impurities detected with NMR Example 5

4,4',4'',4'''-(6-(dibutylamino)-1,3,5-triazine-2,4-diyl)bis(azanetriyl)tetrakis-(methylene)-tetrakis(2,6-di-tert-butylphenol) ($C_{71}H_{110}N_6O_4$): Structure (16)

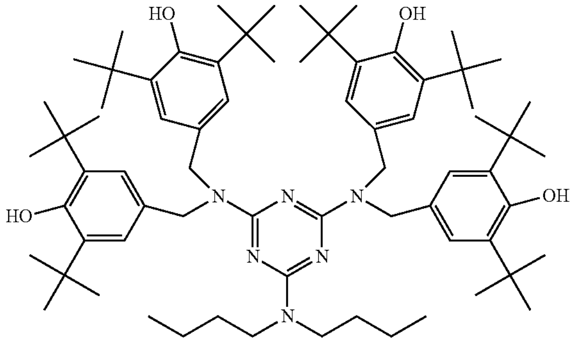 [SMILES: CCCCN(CCCC)c1nc(N(Cc2cc(C(C)(C)C)c(O)c(C(C)(C)C)c2)Cc2cc(C(C)(C)C)c(O)c(C(C)(C)C)c2)nc(N(Cc2cc(C(C)(C)C)c(O)c(C(C)(C)C)c2)Cc2cc(C(C)(C)C)c(O)c(C(C)(C)C)c2)n1]

In a 500 $cm^3$ three-necked round bottom flask, equipped with a thermometer and a condenser, 34.66 g (168 mmol) 2,6-Di-tert-butyl phenol were dissolved in 60 $cm^3$ acetonitrile. Then, 7.5 ml (92.4 mmol) aqueous formaldehyde solution (37%) were added, the reaction mixture was intensively mixed, followed by the addition of 10 g (42 mmol) N,N-dibutyl-1,3,5-triazine-2,4,6-triamine. Adjacent, 45.0 $cm^3$ (960 mmol) formic acid (98%) were added rapidly and the mixture was stirred in an 80° C. pre-tempered oil bath for seven hours. Evaporation of the reaction medium and recrystallisation in 2-propanol afforded the product as a white crystalline substance greater than 94%.

Purification of the Crude Product:

Crystallization from 2-propanol:

The raw product was dissolved in 2-propanol and the solution was allowed to stand at room temperature without cover. The separated precipitate was filtered (sintered glass suction strainer, A2) and washed with small portions of cold 2-propanol.

Characterisation of Structure (16):

Mp.: 236° C., Decomposition temperature: 327° C.

HPLC/MS: >94% without response factor correction

All signals show magnetic in-equivalent environments of approximately equal intensity.

$^1$H NMR (400 MHz, $CDCl_3$, 30° C.): δ=7.15-7.08 (s, 8H, Ar—H), 5.05-5.03 (s, 4H, —OH), 4.71-4.68 (s, 8H, —N—$CH_2$—Ar), 3.49 (t, 4H, —N—$CH_2$—$CH_2$—$CH_2$—$CH_3$), 1.53-1.45 (m, 8H, —N—$CH_2$—$CH_2$—$CH_2$—$CH_3$), 1.41-1.36 (s, 72H, —C—$(CH_3)_3$), 0.78-0.75 (m, 8H, —N—$CH_2$—$CH_2$—$CH_2$—$CH_3$) ppm

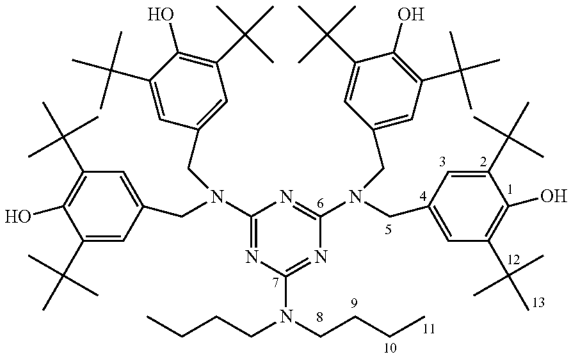 [SMILES: CCCCN(CCCC)c1nc(N(Cc2cc(C(C)(C)C)c(O)c(C(C)(C)C)c2)Cc2cc(C(C)(C)C)c(O)c(C(C)(C)C)c2)nc(N(Cc2cc(C(C)(C)C)c(O)c(C(C)(C)C)c2)Cc2cc(C(C)(C)C)c(O)c(C(C)(C)C)c2)n1]

$^{13}$C NMR (100 MHz, $CDCl_3$, 30° C.): δ=166.13, 165.47, 152.56, 152.46, 135.50, 135.42, 130.13, 125.37, 124.61 (C1, C2, C3, C4, C6, C7), 48.02, 46.45 (C5, C8), 34.23, 34.20 (C12), 30.39, 30.36 (C9, C13), 20.27 (C10), 13.97 (C11) ppm FT-IR (ν): 3903, 3751, 3690, 3633, 3068, 3004, 2954, 2870, 2364, 1802, 1529, 1488, 1423, 1398, 1360, 1342, 1318, 1303, 1232, 1209, 1173, 1157, 1121, 1023, 976, 959, 930, 884, 848, 808, 785, 770, 730, 707, 683, 655, 614 $cm^{-1}$ Elemental Analysis (calc.): C, 76.71; H, 9.97; N, 7.56.

Elemental Analysis (meas.): C, 76.87; H, 9.88; N, 7.96.

Example 6

4,4',4'',4'''-(6-phenyl-1,3,5-triazine-2,4-diyl)bis(azanetriyl)tetrakis(methylene)tetrakis-(2,6-di-tert-butylphenol) ($C_{69}H_{97}N_5O_4$): Structure (17)

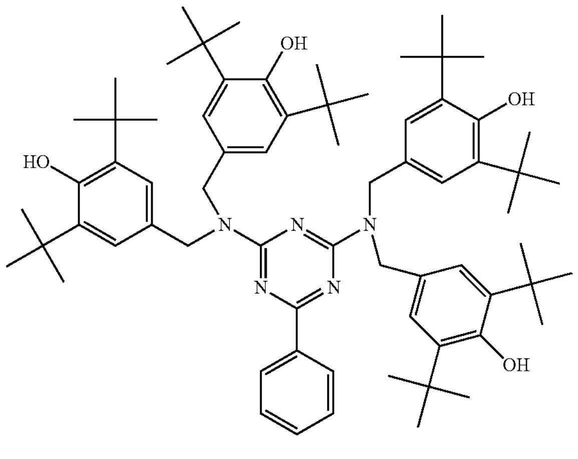 [SMILES: CC(C)(C)c1cc(CN(Cc2cc(C(C)(C)C)c(O)c(C(C)(C)C)c2)c2nc(-c3ccccc3)nc(N(Cc3cc(C(C)(C)C)c(O)c(C(C)(C)C)c3)Cc3cc(C(C)(C)C)c(O)c(C(C)(C)C)c3)n2)cc(C(C)(C)C)c1O]

In a 500 $cm^3$ three-necked round bottom flask, equipped with a thermometer and a condenser, 69.32 g (336 mmol) 2,6-Di-tert-butyl phenol were dissolved in 120 $cm^3$ acetonitrile. Then, 15 ml (184.8 mmol) aqueous formaldehyde solution (37%) were added, the reaction mixture was intensively mixed, followed by the addition of 7.85 g (42 mmol) Benzoguanamin (C-1655). Adjacent, 90 $cm^3$ (1.92 mol) formic acid (98%) were added rapidly and the mixture was stirred in an 80° C. pre-tempered oil bath for seven hours.

Purification of the Crude Product:

Crystallization from 2-propanol:

The raw product was dissolved in 2-propanol and the solution was allowed to stand at room temperature without cover. The separated precipitate was filtered (sintered glass suction strainer, A2) and washed with small portions of cold 2-propanol.

Characterisation of Structure (17):

Mp.: 218° C., Decomposition temperature: 352° C.

HPLC/MS: It. HPLC/MS: HPLC/MS: >63% without response factor correction of (x), 27% without response factor correction of 3' (see structure below)

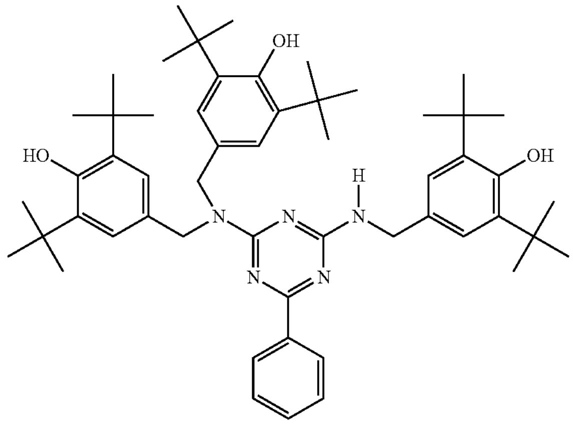

Chemical Formula: $C_{54}H_{75}N_5O_3$
Molecular Weight: 842.21

All signals show magnetic in-equivalent environments of approximately equal intensity.

$^1$H NMR (400 MHz, $CDCl_3$, 30° C.): δ=8.55-8.53 (m, 2H, Ar—H), 7.46-7.39 (m, 3H, Ar—H), 7.24-7.11 (s, 8H, Ar—H), 5.11-5.06 (s, 4H, —OH), 4.87-4.73 (s, 8H, —N—$CH_2$—Ar), 1.39-1.36 (s, 72H, —C—$(CH_3)_3$) ppm

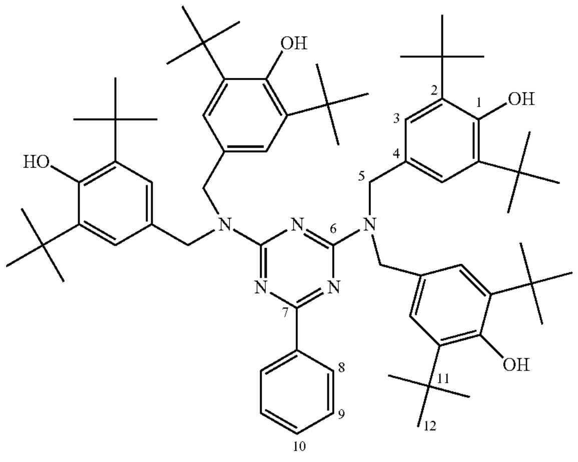 [SMILES: CC(C)(C)c1cc(CN(Cc2cc(C(C)(C)C)c(O)c(C(C)(C)C)c2)c2nc(-c3ccccc3)nc(N(Cc3cc(C(C)(C)C)c(O)c(C(C)(C)C)c3)Cc3cc(C(C)(C)C)c(O)c(C(C)(C)C)c3)n2)cc(C(C)(C)C)c1O]

$^{13}$C NMR (100 MHz, $CDCl_3$, 30° C.): δ=169.99, 166.22, 152.88, 152.78, 137.93, 135.77, 135.71, 130.89, 129.63, 129.22, 128.43, 127.94, 125.27, 124.97 (C1, C2, C3, C4, C6, C7, C8, C9, C10), 48.56, 48.45 (C5), 34.26, 34.21 (C11), 30.34, 30.32 (C12) ppm FT-IR (ν): 3853, 3750, 3632, 2954, 2870, 2362, 1590, 1532, 1483, 1423, 1389, 1360, 1304, 1232, 1208, 1157, 1120, 1024, 975, 959, 885, 847, 809, 781, 770, 705, 613 $cm^{-1}$ Elemental Analysis: C, 78.14; H, 9.22; N, 6.60
Elemental Analysis (meas.): C, 77.56; H, 9.4; N, 6.67

Example 7

4,4',4'',4'''-(6-(bis(hydroxymethyl)amino)-1,3,5-triazine-2,4-diyl)bis(azanetriyl)tetrakis-(methylene)tetrakis(2,6-di-tert-butylphenol): Structure (18)

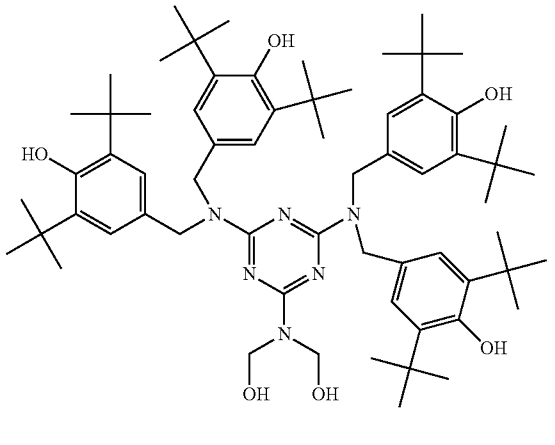 [SMILES: CC(C)(C)c1cc(CN(Cc2cc(C(C)(C)C)c(O)c(C(C)(C)C)c2)c2nc(N(CO)CO)nc(N(Cc3cc(C(C)(C)C)c(O)c(C(C)(C)C)c3)Cc3cc(C(C)(C)C)c(O)c(C(C)(C)C)c3)n2)cc(C(C)(C)C)c1O]

In a 500 $cm^3$ three-necked round bottom flask, equipped with a thermometer and a condenser, 86.65 g (420 mmol) 2,6-Di-tert-butyl phenol were dissolved in 60 $cm^3$ acetonitrile. Then, 21.1 ml (260 mmol) aqueous formaldehyde solution (37%) were added, the reaction mixture is intensively mixed, followed by the addition of 11.6 g (42 mmol) 6-(hydroxymethylamino)-1,3,5-triazine-2,4-diyl)bis(azanetriyl)tetramethanol. Adjacent, 45.0 $cm^3$ (960 mmol) formic acid (98%) were added rapidly and the mixture was stirred in an 80° C. pre-tempered oil bath for seven hours. After cooling down the product was filtered off, the filtrate was treated with NaOH to a pH of 7.

Purification of the Crude Product:

Crystallization from 2-propanol:

The raw product was dissolved in 2-propanol and the solution was allowed to stand at room temperature without cover. The separated precipitate was filtered (sintered glass suction strainer, A2) and washed with small portions of cold 2-propanol.

Characterisation of Structure (18):

Mp.: melting under decomposition at 330° C.

HPLC/MS: product has only poor solubility, according to MS analysis the product has high purity; insoluble parts have been removed with a filter syringe.

FT-IR (v): 3638, 2961, 2873, 1527, 1491, 1434, 1418, 1391, 1359, 1341, 1312, 1274, 1252, 1231, 1207, 1177, 1156, 1122, 1024, 977, 960, 871, 851, 809, 785, 770, 715, 681, 608 $cm^{-1}$

Elemental Analysis: C, 73.68; H, 9.32; N, 7.93;

Elemental Analysis (meas.): C, 73.56; H, 9.4; N, 7.73

Example 8

Testing of Compounds of Example 4 to 7 as Antioxidant in PP Powder

8a) Compounding by Using a Rheomix 540 OS

Neat PP powder from Borealis (HD 120) was used to produce different compounds with Ca-Stearate as a filler (C1: pure PP+Ca-Stearate). Additionally the compounds of Example 4 to 7 were added to C1 in different amounts as well as two commercially antioxidant types (Irganox 1010, Irganox 3114). Table 2 shows the composition of the different compounds.

TABLE 2 compositions processed via kneading using Rheomix 540 OS

| | Ca-Stearate [w %] | Irganox 1010 [w %] | Irganox 3114 [w %] | Ex. 4 [w %] | Ex. 5 [w %] | Ex. 6 [w %] | Ex. 7 [w %] |
|---|---|---|---|---|---|---|---|
| C1 | 0.05 | — | — | — | — | — | — |
| C2 | 0.05 | 0.05 | — | — | — | — | — |
| C3 | 0.05 | — | 0.05 | — | — | — | — |
| C4 | 0.05 | — | — | 0.05 | — | — | — |
| C5 | 0.05 | — | — | 0.1 | — | — | — |
| C6 | 0.05 | — | — | 0.15 | — | — | — |
| C7 | 0.05 | — | — | — | 0.05 | — | — |
| C8 | 0.05 | — | — | — | 0.1 | — | — |
| C9 | 0.05 | — | — | — | 0.15 | — | — |
| C10 | 0.05 | — | — | — | — | 0.05 | — |
| C11 | 0.05 | — | — | — | — | 0.1 | — |
| C12 | 0.05 | — | — | — | — | 0.15 | — |
| C13 | 0.05 | — | — | — | — | — | 0.05 |
| C14 | 0.05 | — | — | — | — | — | 0.1 |
| C15 | 0.05 | — | — | — | — | — | 0.15 |

TABLE 3 oxygen induction time (OIT) according to Variant 2

| | OIT/min |
|---|---|
| C1 | 3.6 |
| C3 | 3.7 |
| C4 | 3.9 |
| C7 | 4.4 |

TABLE 3-continued oxygen induction time (OIT) according to Variant 2

| | OIT/min |
|---|---|
| C10 | 4.4 |
| C13 | 4.7 |

As can be seen from Table 3, the inventive use of the compounds of Example 4 to 7 show higher OIT times than commercially available antioxidant Irganox 3114, thus being more effective compared to Irganox 3114.

In FIG. 2 the result of the viscosity measurement is shown. As can be easily seen the inventive use of the compounds of Example 4 to 7 in compositions C4, C7, C10 and C13 show clearly better results than compositions C2 and C3 using commercially available antioxidants Irganox 1010 and Irganox 3114.

8b) Compounding by Multiple Extrusion

TABLE 4

Composition of the compounds processed via multiple extrusion

| | Ca-Stearate [w %] | Irganox 1010 [w %] | Irganox 3114 [w %] | Ex. 4 [w %] | Ex. 5 [w %] | Ex. 6 [w %] | Ex. 7 [w %] |
|---|---|---|---|---|---|---|---|
| C1* | 0.05 | — | — | — | — | — | — |
| C2* | 0.05 | 0.05 | — | — | — | — | — |
| C3* | 0.05 | — | 0.05 | — | — | — | — |
| C4* | 0.05 | — | — | 0.05 | — | — | — |
| C7* | 0.05 | — | — | — | 0.05 | — | — |
| C10* | 0.05 | — | — | — | — | 0.05 | — |
| C13* | 0.05 | — | — | — | — | — | 0.05 |

TABLE 5

OIT after first extrusion, MFR after $1^{st}$, $2^{nd}$, $3^{rd}$, $4^{th}$ and $5^{th}$ extrusion cycle

| | OIT/min | MFR $1^{st}$ cycle | MFR $2^{nd}$ cycle | MFR $3^{rd}$ cycle | MFR $4^{th}$ cycle | MFR $5^{th}$ cycle |
|---|---|---|---|---|---|---|
| C1* | 3.6 | 4.4 | 11.2 | 27.2 | 30.2 | 42.7 |
| C2* | 6.2 | 1.9 | 4.1 | 7.1 | 10.3 | 14.4 |
| C3* | 5.0 | 2.2 | 4.9 | 8.5 | 14.7 | 19.5 |
| C4* | 6.1 | 1.5 | 3.4 | 5.7 | 9.7 | 11.9 |
| C7* | 5.1 | 1.4 | 3.2 | 5.4 | 8.6 | 12.4 |
| C10* | 5.6 | 1.1 | 4.1 | 7.2 | 10.6 | 14.7 |
| C13* | 7.7 | 1.2 | 2.6 | 4.2 | 6.3 | 8.6 |

As can be seen easily from Table 5 the inventive use of the compounds of Example 4 to 7 in compositions C4, C7, C10 and C13 show clearly better results than compositions C2 and C3 using commercially available antioxidants Irganox 1010 and Irganox 3114, as compositions C4, C7, C10 and C13 have less increase in MFR compared to compositions C2 and C3.

The invention claimed is:

1. A method of stabilizing one or more polyolefins against degradation comprising the step of incorporating into said material an amino-triazine based Mannich-compound according to formula (I)

(I)

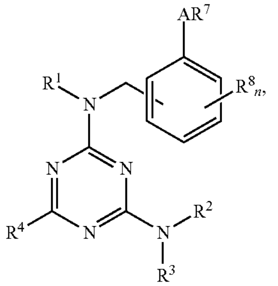

dimers or trimers and precondensate therefrom according to formula (II)

(II)

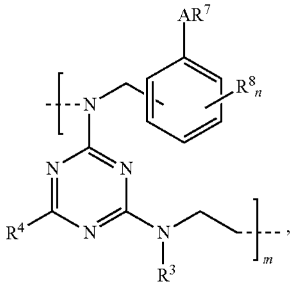

or mixtures thereof, in an amount effective to stabilize said organic material, wherein A is O, N or S, $R^4$ is hydrogen or $Q^1$ or a group $R^5$—N—$R^6$ bonded with its central nitrogen atom to the triazine ring of structure (I) or (II), $R^1$, $R^2$, $R^3$, $R^5$ and $R^6$ are hydrogen, or $Q^1$ or group of the formula (III)

(III)

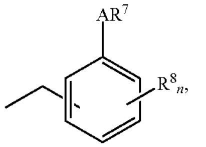

$R^7$ is hydrogen or $Q^1$, wherein when A is O or S, $R^7$ is present once, and when A is N, $R^7$ is present twice, each $R^8$ is independently selected from another and can be $Q^1$, or is selected from a group consisting of substituted or non-substituted hydroxyl; substituted or non-substituted amino; halogen; substituted or non-substituted sulphur; and a group with the structure of (IV), (IV)

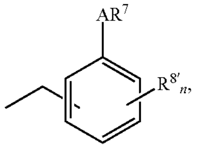

whereby $R^{8'}$ has the meaning of $R^8$ whereby $R^{8'}$ is not also structure (IV), n is 1 or 2, whereby the position of $R^8{}_n$ is ortho to $AR^7$, $Q^1$ is selected from the group consisting of substituted and non-substituted, linear or branched $C_1$-$C_{50}$-alkyl, substituted and non-substituted, linear or branched $C_2$-$C_{50}$-alkenyl, substituted and non-substituted, linear or branched $C_2$-$C_{50}$-alkinyl, substituted and non-substituted $C_3$-$C_{10}$-cycloalkyl, substituted and non-substituted $C_5$-$C_7$-cycloalkenyl, and substituted and non-substituted $C_6$-$C_{20}$-aryl, which in each case can be interrupted by one or more atoms or groups selected from the group consisting of oxygen atoms, sulphur atoms, substituted nitrogen atoms, double bonds, siloxan groups and/or by one or more groups of the type —C(O)O—, —OC(O)—, —C(O)—, —C(O)NH—, —OC(O)NH—, and/or —OC(O)O—, wherein in case of $R^4$ the atoms and groups selected from oxygen atoms, sulphur atoms, —OC(O)—, —C(O)—, —NHC(O)O—, —NHC(O)NH— or —OC(O)O— can be directly connected to the triazine ring and in case of $R^7$ the atoms and groups selected from —C(O)—, C(O)O— or —C(O)NH— can be directly connected to A and in case of $R^8$ the groups selected from —OC(O)—, —C(O)—, —NHC(O)O—, —NHC(O)NH—, —C(O)O—, —C(O)NH— or —OC(O)O— can be directly connected to the aromatic ring, m is 2 to 20.

2. The method of claim 1, wherein in the formula (I) and (II):

A is O or N, $R^4$ is $Q^1$, $Q^1$ being selected from the group consisting of substituted or non-substituted, linear or branched $C_1$-$C_{18}$-alkyl; substituted or non-substituted $C_6$-$C_{10}$-aryl; or a group $R^5$—N—$R^6$ bonded with its central nitrogen atom to the triazine ring of structure (I) or (II), with $R^5$ and $R^6$ being selected from the group consisting of hydrogen; substituted or non-substituted, linear or branched $C_1$-$C_{12}$-alkyl; substituted or non-substituted $C_3$-$C_7$-cycloalkyl; and substituted or non-substituted, linear or branched $C_2$-$C_{12}$-alkenyl, $R^1$, $R^2$ and $R^3$ are selected from the group consisting of hydrogen, substituted or non-substituted, linear or branched $C_1$-$C_{18}$-alkyl, substituted or non-substituted $C_3$-$C_7$-cycloalkyl, substituted or non-substituted, linear or branched $C_2$-$C_{12}$-alkenyl, and the group of the formula (III)

(III)

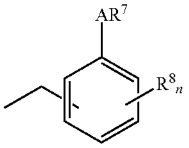

$R^7$ is one of hydrogen or $C_1$-$C_{12}$-alkyl which can be interrupted by one or more oxygen atoms, substituted nitrogen atoms, and/or by one or more groups of the type —C(O)O—, —OC(O)— and —C(O)—, whereby the group —C(O)— can also be directly connected to A, $R^8$ is selected from the group consisting of —OH; $—OCH_3$; $—OC_2H_5$; $—NH_2$; substituted or non-substituted, linear or branched $C_1$-$C_{12}$-alkyl; substituted and with $m_{21}$ being a number from 1 to 20.

In the compound (101), the terminal group bonded to the silicon atom can be, for example, $(CH_3)_3Si$—O—, and the terminal group bonded to the oxygen can be, for example, $—Si(CH_3)_3$. The compounds (101) can also be in the form of cyclic compounds if $m_{21}$ is a number from 3 to 10, i.e. the free valences shown in the structural formula then form a direct bond. non-substituted $C_3$-C7-cycloalkyl; substituted and non-substituted, linear or branched $C_2$-$C_{12}$-alkenyl; and substituted and non-substituted $C_6$-$C_{12}$ aryl, m is 2 to 10.

3. The method of claim 1, wherein said compounds of formula (I) and (II) are selected from the group consisting of:
(1)
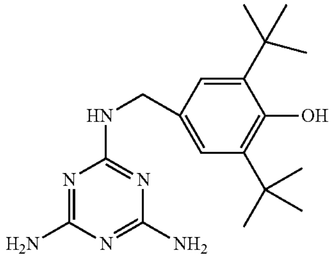
(2)
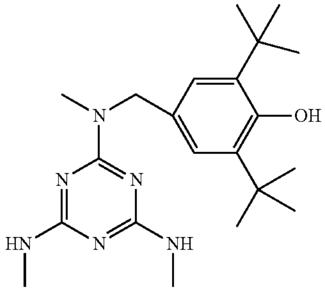
(3)
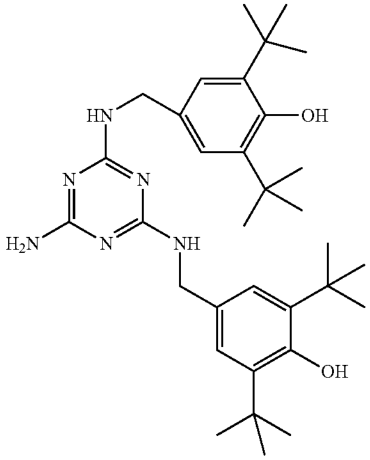
(4)
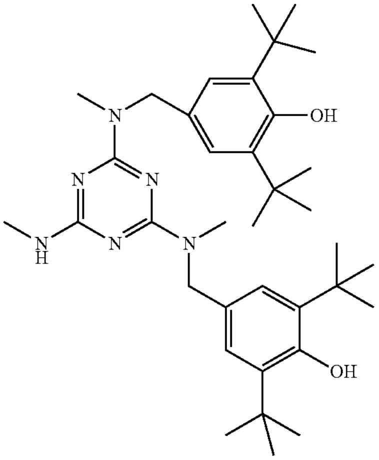
(5)
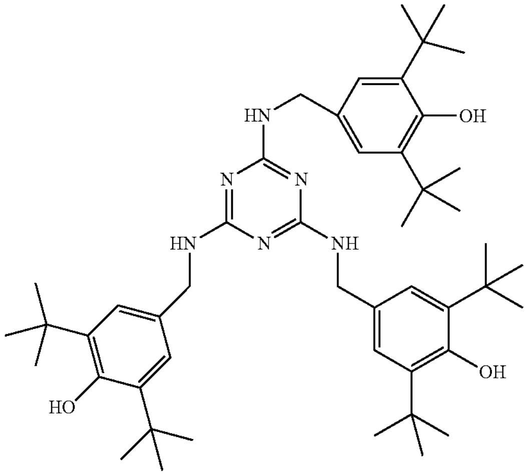
(6)
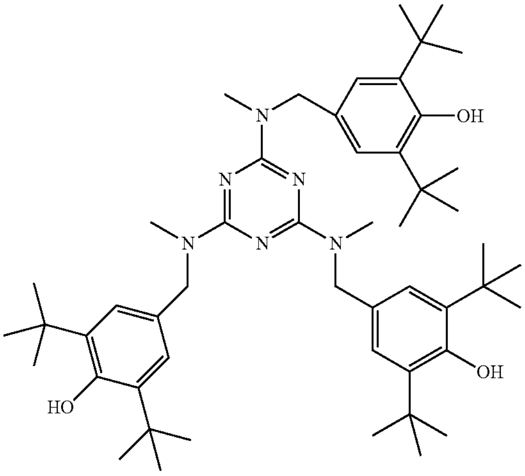

-continued
(7)
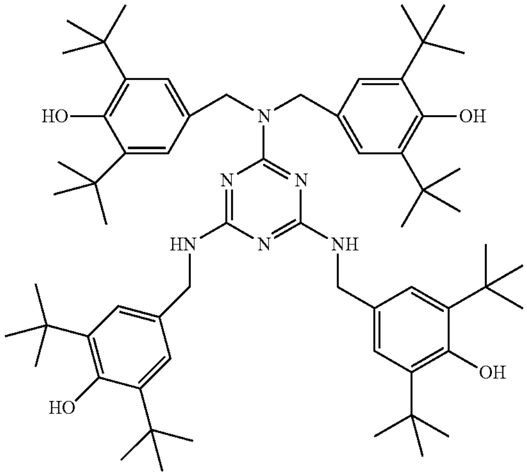
(8)
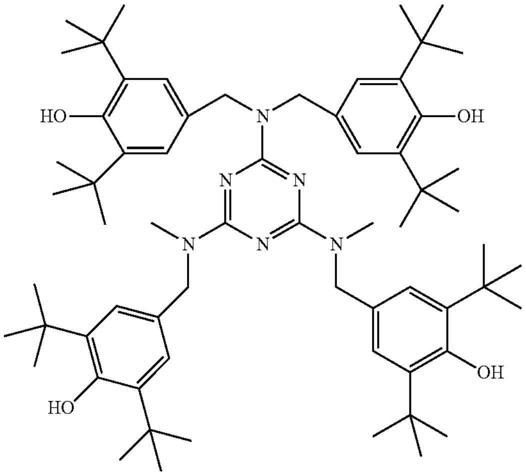
(9)
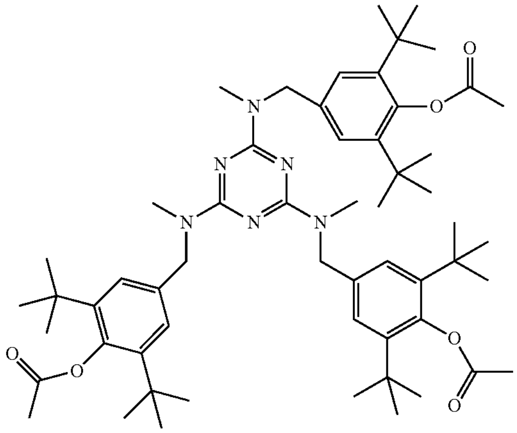
(10)
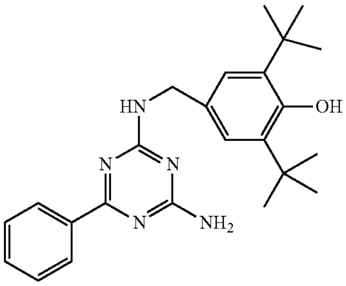
(11)
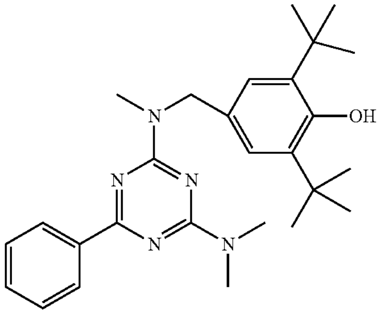
(12)
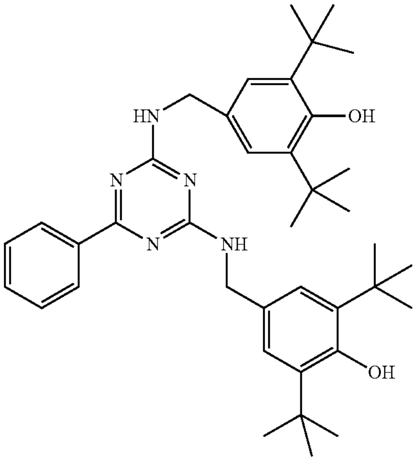

-continued
(13)
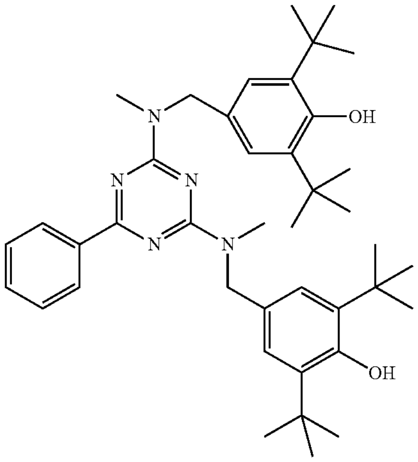
(14)
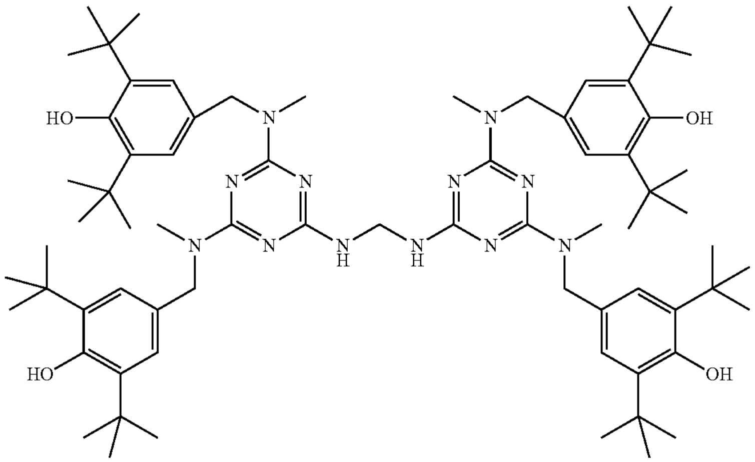
(15)
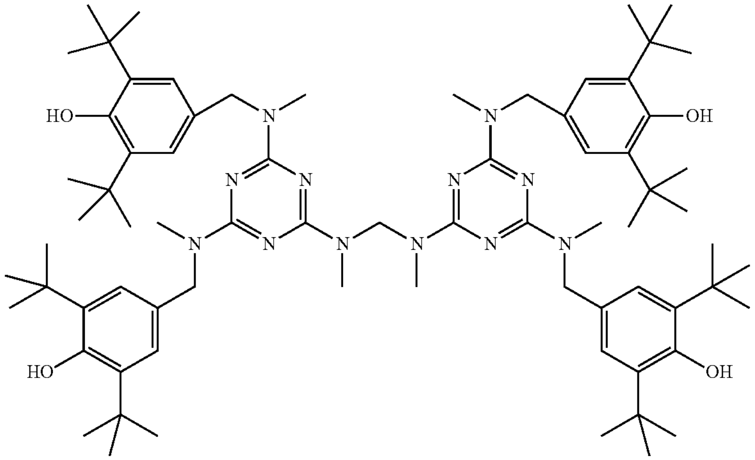

-continued (16)

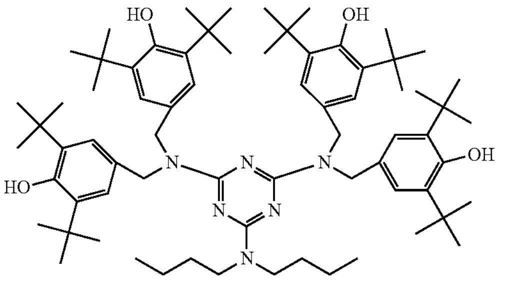

(17)

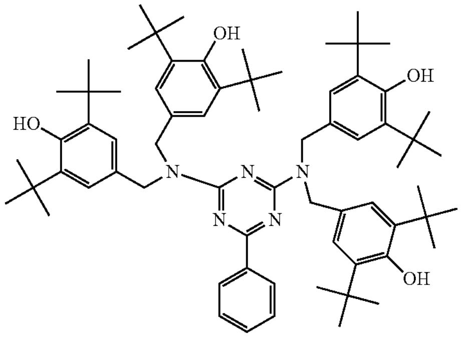

(18)

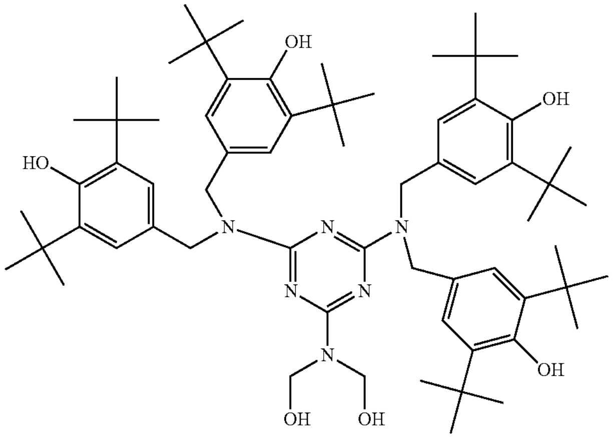

and combinations thereof.

4. The method of claim 1, wherein said degradation is oxidative degradation.

5. The method of claim 1, wherein said degradation is ultraviolet degradation.

6. The method of claim 1, further comprising the step of introducing one or more hindered amine light stabilizers to said organic material with said amino-triazine based Mannich-compound.

7. A method of stabilizing one or more polyolefins against oxidative and ultraviolet degradation comprising the step of incorporating into said material an amino-triazine based Mannich-compound according to formula (I)

(I)

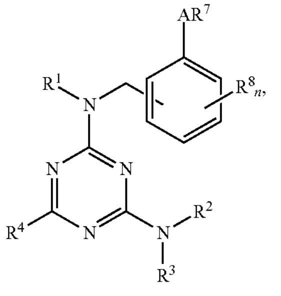

dimers or trimers and precondensate therefrom according to formula (II)

(II)

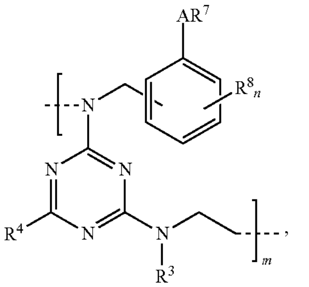

or mixtures thereof, in an amount effective to stabilize said organic material, wherein A is O, N or S, $R^4$ is hydrogen or $Q^1$ or a group $R^5$—N—$R^6$ bonded with its central nitrogen atom to the triazine ring of structure (I) or (II), $R^1$, $R^2$, $R^3$, $R^5$ and $R^6$ are hydrogen, or $Q^1$ or group of the formula (III)

(III)

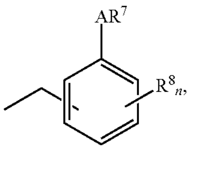

$R^7$ is hydrogen or $Q^1$, wherein when A is O or S, $R^7$ is present once, and when A is N, $R^7$ is present twice, each $R^8$ is independently selected from another and can be $Q^1$, or is selected from the group consisting of substituted or non-substituted hydroxyl; substituted or non-substituted amino; halogen; substituted or non-substituted sulphur; and a group with the structure of (IV), (IV)

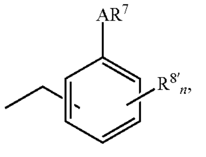

whereby $R^{8'}$ has the meaning of $R^8$ whereby $R^{8'}$ is not also structure (IV), n is 1 or 2, whereby the position of $R^8{}_n$ is ortho to $AR^7$, $Q^1$ is selected from the group consisting of substituted and non-substituted, linear or branched $C_1$-$C_{50}$-alkyl, substituted and non-substituted, linear or branched $C_2$-$C_{50}$-alkenyl, substituted and non-substituted, linear or branched $C_2$-$C_{50}$-alkinyl, substituted and non-substituted $C_3$-$C_{10}$-cycloalkyl, substituted and non-substituted $C_5$-$C_7$-cycloalkenyl, and substituted and non-substituted $C_6$-$C_{20}$-aryl, which in each case can be interrupted by one or more atoms or groups selected from the group consisting of oxygen atoms, sulphur atoms, substituted nitrogen atoms, double bonds, siloxan groups and/or by one or more groups of the type —C(O)O—, —OC(O)—, —C(O)—, —C(O)NH—, —OC(O)NH—, and/or —OC(O)O—, wherein in case of $R^4$ the atoms and groups selected from oxygen atoms, sulphur atoms, —OC(O)—, —C(O)—, —NHC(O)O—, —NHC(O)NH— or —OC(O)O— can be directly connected to the triazine ring and in case of $R^7$ the atoms and groups selected from —C(O)—, C(O)O— or —C(O)NH— can be directly connected to A and in case of $R^8$ the groups selected from —OC(O)—, —C(O)—, —NHC(O)O—, —NHC(O)NH—, —C(O)O—, —C(O)NH— or —OC(O)O— can be directly connected to the aromatic ring, m is 2 to 20.

8. The method of claim 7, further comprising the step of introducing one or more hindered amine light stabilizers to said organic material with said amino-triazine based Mannich-compound.

9. The method of claim 7, wherein in the formula (I) and (II):

A is O or N, $R^4$ is $Q^1$, $Q^1$ being selected from the group consisting of substituted or non-substituted, linear or branched $C_1$-$C_{18}$-alkyl; substituted or non-substituted $C_6$-$C_{10}$-aryl; or a group $R^5$—N—$R^6$ bonded with its central nitrogen atom to the triazine ring of structure (I) or (II), with $R^5$ and $R^6$ being selected from the group consisting of hydrogen; substituted or non-substituted, linear or branched $C_1$-$C_{12}$-alkyl; substituted or non-substituted $C_3$-$C_7$-cycloalkyl; and substituted or non-substituted, linear or branched $C_2$-$C_{12}$-alkenyl, $R^1$, $R^2$ and $R^3$ are selected from the group consisting of hydrogen; substituted or non-substituted, linear or branched $C_1$-$C_{18}$-alkyl; substituted or non-substituted $C_3$-$C_7$-cycloalkyl; substituted or non-substituted, linear or branched $C_2$-$C_{12}$-alkenyl; and the group of formula (III)

(III)

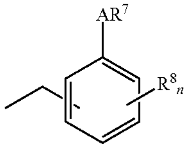

$R^7$ is one of hydrogen or $C_1$-$C_{12}$-alkyl which can be interrupted by one or more oxygen atoms, substituted nitrogen atoms, and/or by one or more groups of the type —C(O)O—, —OC(O)— and —C(O)—, whereby the group —C(O)— can also be directly connected to A, $R^8$ is selected from a group consisting of —OH; —$OCH_3$; —$OC_2H_5$; —$NH_2$; substituted or non-substituted, linear or branched $C_1$-$C_{12}$-alkyl; substituted and non-substituted $C_3$-$C_7$-cycloalkyl; substituted and non-substituted, linear or branched $C_2$-$C_{12}$-alkenyl; and substituted and non-substituted $C_6$-$C_{12}$ aryl, m is 2 to 10.

10. The method of claim 7, wherein said compounds of formula (I) and (II) are selected from the group consisting of:

(1)

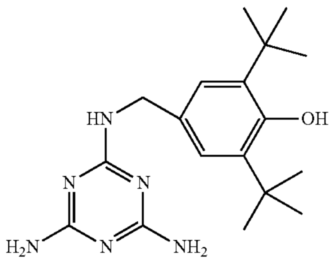

(2)

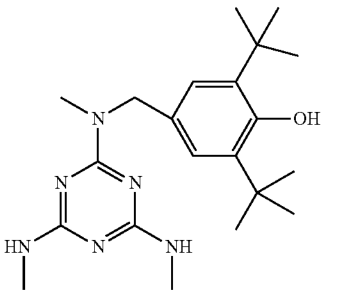

-continued
(3)
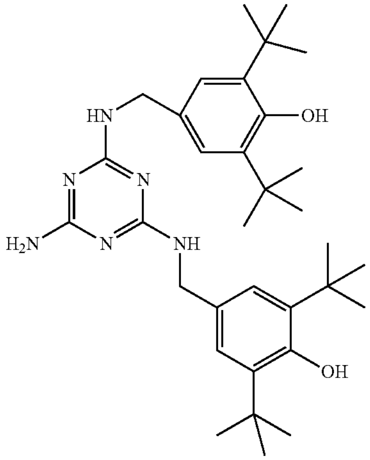
(4)
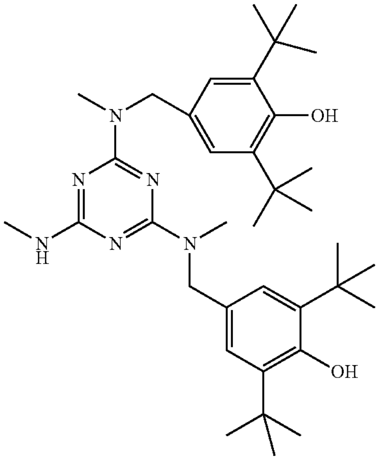
(5)
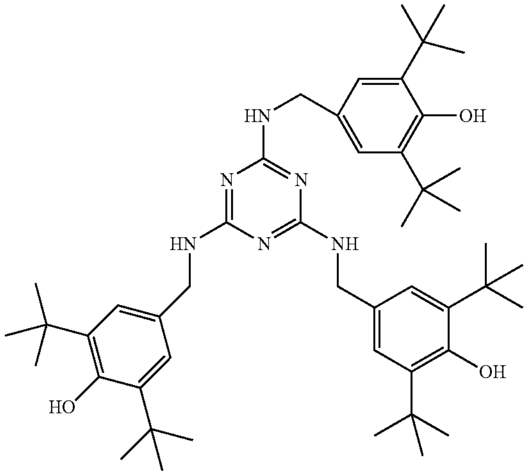
(6)
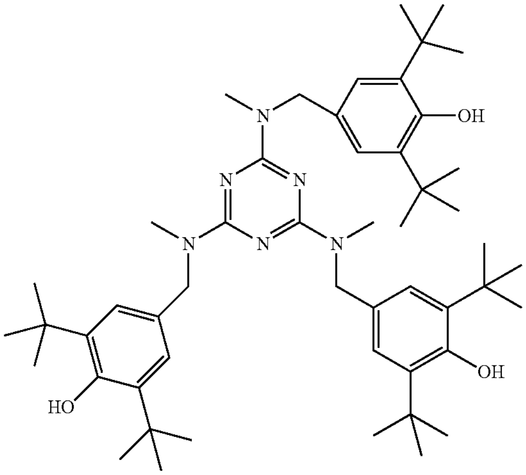
(7)
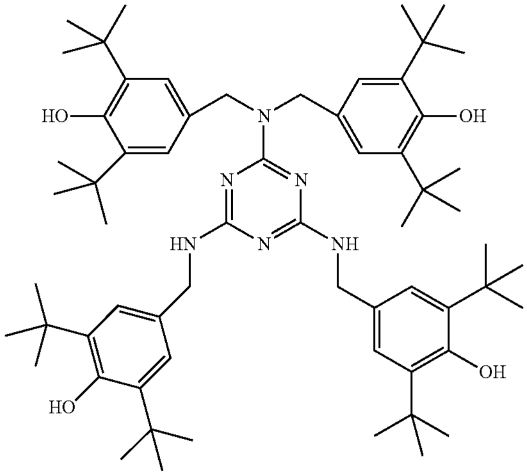
(8)
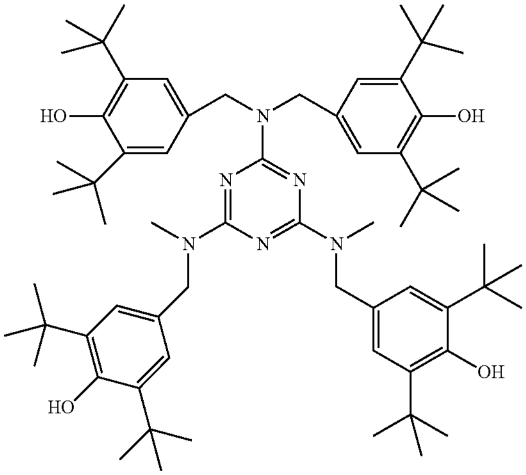

-continued
(9)
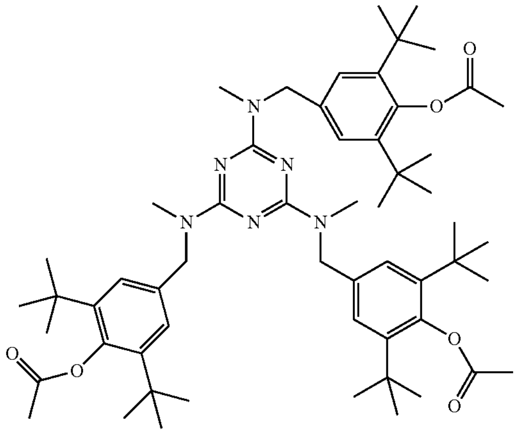
(10)
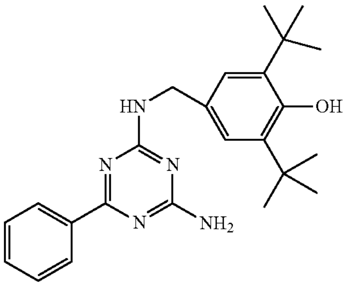
(11)
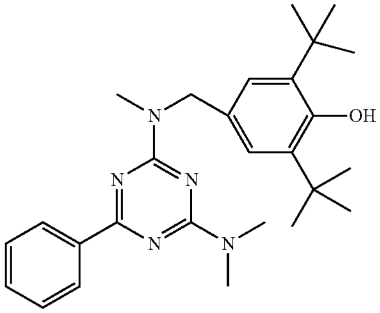
(12)
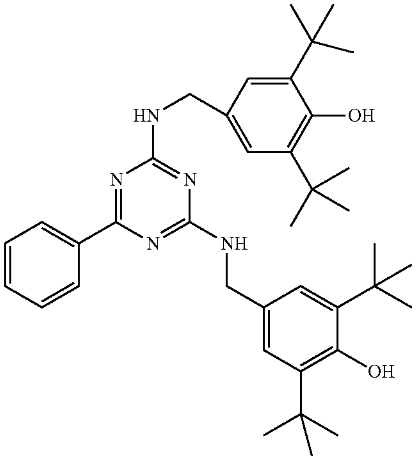
(13)
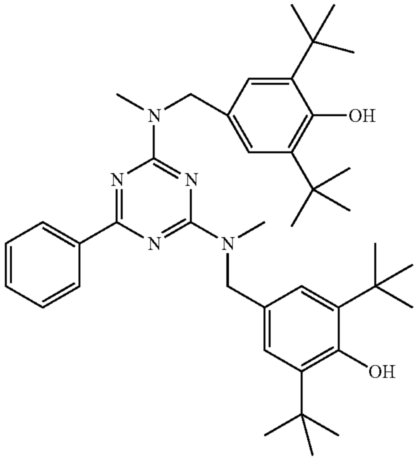

-continued
(14)
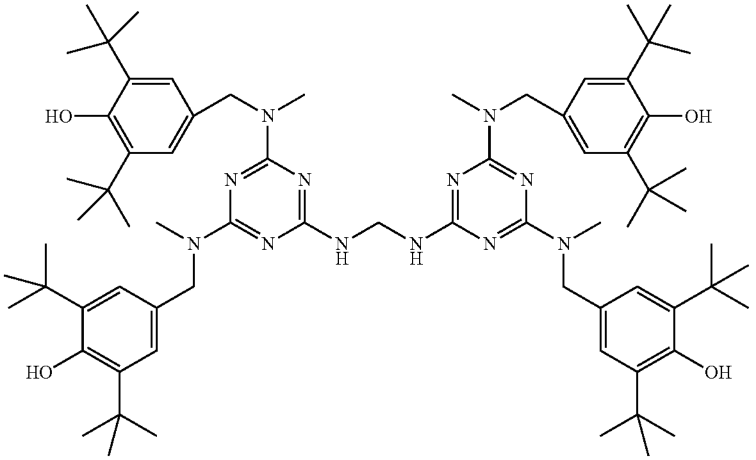
(15)
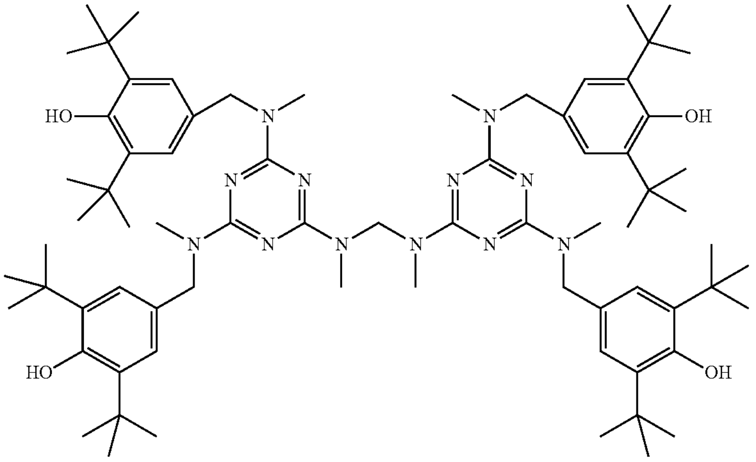
(16)
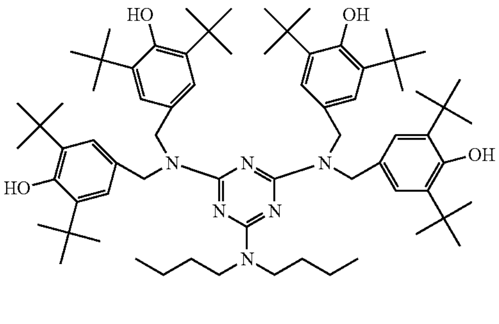
(17)
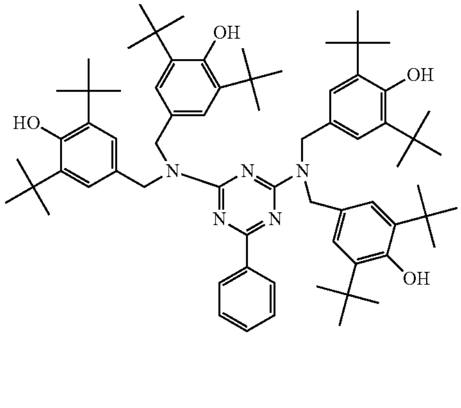

-continued (18)

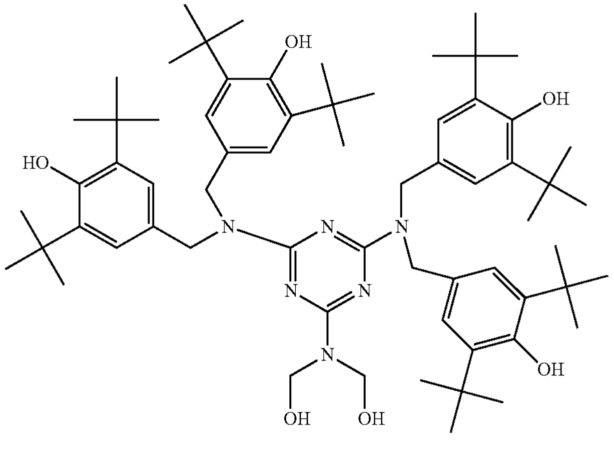

and combinations thereof.

11. The method according to claim 7, wherein the amino-triazine based Mannich-compound is present in the organic material between about 0.05 and 0.15 wt %.

12. A method of stabilizing one or more polyolefins against degradation comprising the step of incorporating into said material an amino-triazine based Mannich-compound according to formula (I)

(I)

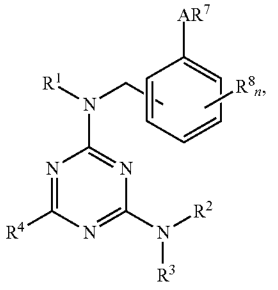

in an amount effective to stabilize said organic material, wherein

A is O, N or S, $R^4$ is hydrogen or $Q^1$ or a group $R^5$—N—$R^6$ bonded with its central nitrogen atom to the triazine ring of structure (I), $R^1$, $R^2$, $R^3$, $R^5$ and $R^6$ are hydrogen, or $Q^1$ or group of the formula (III)

(III)

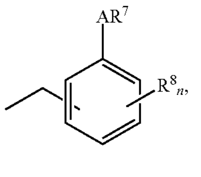

$R^7$ is hydrogen or $Q^1$, wherein when A is O or S, $R^7$ is present once, and when A is N, $R^7$ is present twice, each $R^8$ is independently selected from another and can be $Q^1$, or is selected from a group consisting of substituted or non-substituted hydroxyl; substituted or non-substituted amino; halogen; substituted or non-substituted sulphur; and a group with the structure of (IV), (IV)

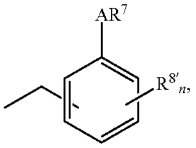

whereby $R^{8'}$ has the meaning of $R^8$ whereby R8' is not also structure (IV), n is 1 or 2, whereby the position of $R^8{}_n$ is ortho to $AR^7$, $Q^1$ is selected from the group consisting of substituted and non-substituted, linear or branched $C_1$-$C_{50}$-alkyl, substituted and non-substituted, linear or branched $C_2$-$C_{50}$-alkenyl, substituted and non-substituted, linear or branched $C_2$-$C_{50}$-alkinyl, substituted and non-substituted $C_3$-$C_{10}$-cycloalkyl, substituted and non-substituted $C_5$-$C_7$-cycloalkenyl, and substituted and non-substituted $C_6$-$C_{20}$-aryl, which in each case can be interrupted by one or more atoms or groups selected from the group consisting of oxygen atoms, sulphur atoms, substituted nitrogen atoms, double bonds, siloxan groups and/or by one or more groups of the type —C(O)O—, —OC(O)—, —C(O)—, —C(O)NH —, —OC(O)NH—, and/or —OC(O)O—, wherein in case of $R^4$ the atoms and groups selected from oxygen atoms, sulphur atoms, —OC(O)—, —C(O)—, —NHC(O)O—, —NHC(O)NH— or —OC(O)O— can be directly connected to the triazine ring and in case of $R^7$ the atoms and groups selected from —C(O)—, C(O)O— or —C(O)NH— can be directly connected to A and in case of $R^8$ the groups selected from —OC(O)—, —C(O)—, —NHC(O)O—, —NHC(O)NH—, —C(O)O—, —C(O)NH— or —OC(O)O— can be directly connected to the aromatic ring, m is 2 to 20.

* * * * *

UNITED STATES PATENT AND TRADEMARK OFFICE

CERTIFICATE OF CORRECTION

PATENT NO. : 9,546,261 B2
APPLICATION NO. : 14/346508
DATED : January 17, 2017
INVENTOR(S) : Rene Dicke et al.

It is certified that error appears in the above-identified patent and that said Letters Patent is hereby corrected as shown below:

In the Claims

Column 74, Lines 58-64, Claim 2, after "substituted and" delete "with $m_{21}$ being a number from 1 to 20.
In the compound (101), the terminal group bonded to the silicon atom can be, for example, $(CH_3)_3Si$-O-, and the terminal group bonded to the oxygen can be, for example, -$Si(CH_3)_3$.
The compounds (101) can also be in the form of cyclic compounds if $m_{21}$ is a number from 3 to 10, i.e. the free valences shown in the structural formula then form a direct bond."

Column 74, Line 64, Claim 2, delete "$C_3$-C7-cycloalkyl;" and insert -- $C_3$-$C_7$-cycloalkyl; --

Column 92, Line 52, Claim 12, delete "-C(O)NH -," and insert -- -C(O)NH-, --

Signed and Sealed this
Eleventh Day of April, 2017

Michelle K. Lee
*Director of the United States Patent and Trademark Office*